(12) United States Patent
Offenborn et al.

(10) Patent No.: US 10,088,431 B2
(45) Date of Patent: *Oct. 2, 2018

(54) METHOD AND SYSTEM FOR OPTICALLY INSPECTING HEADED MANUFACTURED PARTS

(71) Applicant: GII Acquisition, LLC, Davisburg, MI (US)

(72) Inventors: Robert Joseph Offenborn, Birch Run, MI (US); Christopher Michael Alexander, Fenton, MI (US); Gregory Martin Nygaard, Clarkston, MI (US); Michael George Nygaard, Grand Blanc, MI (US)

(73) Assignee: GII Acquisition, LLC, Davisburg, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/636,996

(22) Filed: Jun. 29, 2017

(65) Prior Publication Data

US 2017/0307538 A1  Oct. 26, 2017

Related U.S. Application Data

(63) Continuation-in-part of application No. 15/501,033, filed as application No. PCT/US2015/034349 on Jun.
(Continued)

(51) Int. Cl.
  *G01N 21/00* (2006.01)
  *G01N 21/88* (2006.01)
  (Continued)

(52) U.S. Cl.
  CPC ............ *G01N 21/88* (2013.01); *B07C 5/342* (2013.01); *F42B 35/00* (2013.01); *G01N 21/909* (2013.01);
  (Continued)

(58) Field of Classification Search
  CPC .............. G01N 21/9501; G01N 21/94; G01N 21/8806; G01N 21/956; G01N 21/95607
  (Continued)

(56) References Cited

U.S. PATENT DOCUMENTS 2,645,343 A   7/1953  Nemir
3,411,009 A  11/1968  Ford et al.
(Continued)

FOREIGN PATENT DOCUMENTS

EP     0047936 A1    3/1982
JP   2008073653 A    4/2008
(Continued)

OTHER PUBLICATIONS

International Search Report and Written Opinion, International Application No. PCT/US2012/037892; dated Nov. 19, 2013.
(Continued)

*Primary Examiner* — Md M Rahman
(74) *Attorney, Agent, or Firm* — Brooks Kushman P.C.

(57) ABSTRACT

A method and system for optically inspecting parts are provided wherein the system includes a part transfer subsystem including a transfer mechanism adapted to receive and support a part at a loading station and to transfer the supported part by a split belt conveyor so that the part travels along a first path which extends from the loading station to an inspection station at which the part has a predetermined position and orientation for inspection. An illumination assembly simultaneously illuminates a plurality of exterior side surfaces of the part with a plurality of separate beams of radiation. A telecentric lens and detector assembly forms an optical image of at least a portion of each of the illuminated side surfaces of the part and detects the optical images. A processor processes the detected optical images to obtain a plurality of views of the part which are angularly spaced about the part.

(Continued)

In an alternative embodiment the method and system for optically inspecting headed manufactured parts employ an inclined split track to cause the part to traverse an inspection station by gravity feed. The part is inspected for conformity to dimensional and visual standards and sorted under control of a processor based on images of the part obtained from occluded light and reflected light while the part is within the inspection station.

34 Claims, 21 Drawing Sheets

Related U.S. Application Data 5, 2015, which is a continuation of application No. 14/449,361, filed on Aug. 1, 2014, now Pat. No. 9,228,957, application No. 15/636,996, which is a continuation-in-part of application No. 13/414,081, filed on Mar. 7, 2012, and a continuation-in-part of application No. 15/132,450, filed on Apr. 19, 2016, now Pat. No. 9,697,596, which is a continuation-in-part of application No. 14/629,527, filed on Feb. 24, 2015, now Pat. No. 9,575,013, which is a continuation-in-part of application No. 14/050,907, filed on Oct. 10, 2013, now Pat. No. 9,019,489, which is a continuation of application No. 13/109,369, filed on May 17, 2011, now Pat. No. 8,570,504, application No. 15/636,996, which is a continuation of application No. 13/109,393, filed on May 17, 2011, now abandoned.

(51) Int. Cl.
    B07C 5/342    (2006.01)
    F42B 35/00    (2006.01)
    G01N 21/90    (2006.01)
    G01N 21/952   (2006.01)
    G01N 21/95    (2006.01)

(52) U.S. Cl.
    CPC ....... *G01N 21/952* (2013.01); *G01N 21/9515* (2013.01)

(58) Field of Classification Search
    USPC ...................................... 356/237.2
    See application file for complete search history.

(56) References Cited

U.S. PATENT DOCUMENTS

| | | |
|---|---|---|
| 3,604,940 A | 9/1971 | Matthews |
| 3,770,969 A | 11/1973 | Ansevin |
| 3,924,953 A | 12/1975 | Allard |
| 3,941,484 A | 3/1976 | Dreyfus |
| 4,239,969 A | 12/1980 | Haas et al. |
| 4,280,624 A | 7/1981 | Ford |
| 4,315,688 A | 2/1982 | Pryor |
| 4,547,674 A | 10/1985 | Pryor et al. |
| 4,598,998 A | 7/1986 | Kamei et al. |
| 4,636,635 A | 1/1987 | Kronseder |
| 4,644,394 A | 2/1987 | Reeves |
| 4,691,231 A | 9/1987 | Fitzmorris et al. |
| 4,721,388 A | 1/1988 | Takagi et al. |
| 4,825,068 A | 4/1989 | Suzuki et al. |
| 4,831,251 A | 5/1989 | Hanna |
| 4,852,983 A | 8/1989 | Fein |
| 4,906,098 A | 3/1990 | Thomas et al. |
| 4,912,318 A | 3/1990 | Kajiura et al. |
| 4,923,066 A | 5/1990 | Ophir et al. |
| 4,969,746 A | 11/1990 | McConnell et al. |
| 4,970,401 A | 11/1990 | Sadeh et al. |
| 4,983,043 A | 1/1991 | Harding |
| 5,012,117 A | 4/1991 | Karafa et al. |
| 5,024,529 A | 6/1991 | Svetkoff et al. |
| 5,098,031 A | 3/1992 | Hitomi |
| 5,149,980 A | 9/1992 | Ertel et al. |
| 5,164,995 A | 11/1992 | Brooks et al. |
| 5,168,458 A | 12/1992 | Gomes |
| 5,170,306 A | 12/1992 | Gomes |
| 5,291,272 A | 3/1994 | Demisu |
| 5,383,021 A | 1/1995 | Hanna |
| 5,431,289 A | 7/1995 | Hoffman |
| 5,453,877 A | 9/1995 | Gerbe et al. |
| 5,521,707 A | 5/1996 | Castore et al. |
| 5,531,316 A | 7/1996 | Savino |
| 5,546,189 A | 8/1996 | Svetkoff et al. |
| 5,568,263 A | 10/1996 | Hanna |
| 5,608,530 A | 3/1997 | Gates |
| 5,617,209 A | 4/1997 | Svetkoff et al. |
| 5,646,724 A | 7/1997 | Hershline |
| 5,745,236 A | 4/1998 | Haga |
| 5,751,833 A | 5/1998 | Blit |
| 5,815,275 A | 9/1998 | Svetkoff et al. |
| 5,842,060 A | 11/1998 | White et al. |
| 5,847,382 A | 12/1998 | Koch et al. |
| 5,917,926 A | 6/1999 | Leverett |
| 5,975,710 A | 11/1999 | Luster |
| 6,027,568 A | 2/2000 | Wallace et al. |
| 6,038,521 A | 3/2000 | Kanai |
| 6,046,462 A | 4/2000 | Yokajty et al. |
| 6,055,329 A | 4/2000 | Mufti |
| 6,064,756 A | 5/2000 | Beaty |
| 6,098,031 A | 8/2000 | Svetkoff et al. |
| 6,115,175 A | 9/2000 | Maruyama et al. |
| 6,122,045 A | 9/2000 | Pike et al. |
| 6,252,661 B1 | 6/2001 | Hanna |
| 6,285,034 B1 | 9/2001 | Hanna et al. |
| 6,289,600 B1 | 9/2001 | Watts |
| 6,313,948 B1 | 11/2001 | Hanna |
| 6,324,016 B1 | 11/2001 | Luster |
| 6,441,973 B1 | 8/2002 | Ramm et al. |
| 6,525,333 B1 | 2/2003 | Hooker et al. |
| 6,542,580 B1 | 4/2003 | Carver |
| 6,787,724 B2 | 9/2004 | Bennett et al. |
| 6,959,108 B1 | 10/2005 | Bartelt et al. |
| 7,065,242 B2 | 6/2006 | Petrov et al. |
| 7,134,544 B1 | 11/2006 | Kilper et al. |
| 7,245,759 B2 | 7/2007 | Jones, Jr. et al. |
| 7,312,607 B2 | 12/2007 | Nygaard |
| RE39,978 E | 1/2008 | Bieman |
| 7,329,855 B2 | 2/2008 | Katayama et al. |
| 7,363,817 B2 | 4/2008 | Bond et al. |
| 7,403,872 B1 | 7/2008 | St. Onge et al. |
| 7,633,046 B2 | 12/2009 | Spalding |
| 7,633,634 B2 | 12/2009 | Spalding et al. |
| 7,633,635 B2 | 12/2009 | Nygaard et al. |
| 7,684,054 B2 | 3/2010 | Crowther |
| 7,738,088 B2 | 6/2010 | Spalding |
| 7,738,121 B2 | 6/2010 | Spalding |
| 7,755,754 B2 | 7/2010 | Spalding |
| 7,777,900 B2 | 8/2010 | Nygaard et al. |
| 7,796,278 B2 | 9/2010 | Spalding et al. |
| 7,812,970 B2 | 10/2010 | Nygaard |
| 7,920,278 B2 | 4/2011 | Nygaard |
| 8,054,460 B2 | 11/2011 | Agapiou et al. |
| 8,179,434 B2 | 5/2012 | Koval et al. |
| 8,228,493 B2 | 7/2012 | Yagyu et al. |
| 8,390,826 B2 | 3/2013 | Walstra |
| 8,416,403 B2 | 4/2013 | Nygaard |
| 8,570,504 B2 | 10/2013 | Nygaard |
| 8,615,123 B2 | 12/2013 | Dabic |
| 8,723,068 B2 | 5/2014 | Nygaard |
| 2001/0021026 A1 | 9/2001 | Liu |
| 2003/0034227 A1 | 2/2003 | Gerber |
| 2003/0039388 A1 | 2/2003 | Ulrich et al. |
| 2003/0041381 A1 | 3/2003 | Taymon |
| 2003/0151823 A1 | 8/2003 | Okabe |
| 2003/0201211 A1 | 10/2003 | Bennett et al. |
| 2004/0022427 A1 | 2/2004 | Yang et al. |
| 2004/0066505 A1 | 4/2004 | Berg et al. |

(56) References Cited

U.S. PATENT DOCUMENTS

| | | |
|---|---|---|
| 2004/0223143 A1 | 11/2004 | Yasuda et al. |
| 2004/0263957 A1 | 12/2004 | Hirahara et al. |
| 2005/0094867 A1 | 5/2005 | Jones, Jr. et al. |
| 2005/0174567 A1 | 8/2005 | Hanna |
| 2005/0226779 A1* | 10/2005 | Oldham ............... B01L 3/5025 422/400 |
| 2005/0231723 A1* | 10/2005 | Blasenheim ......... B01L 3/5025 356/414 |
| 2006/0109484 A1 | 5/2006 | Akamatsu |
| 2006/0236792 A1 | 10/2006 | Hanna |
| 2007/0223009 A1 | 9/2007 | Erfling et al. |
| 2008/0013820 A1 | 1/2008 | Vertoprakhov et al. |
| 2008/0049235 A1 | 2/2008 | Crowther |
| 2009/0103107 A1 | 4/2009 | Nygaard |
| 2009/0103111 A1 | 4/2009 | Spalding |
| 2009/0103112 A1 | 4/2009 | Nygaard |
| 2009/0107896 A1 | 4/2009 | Gochar, Jr. |
| 2009/0278925 A1 | 11/2009 | Koval et al. |
| 2009/0279083 A1 | 11/2009 | Agapiou |
| 2010/0084245 A1 | 4/2010 | Gonzalez Alemany et al. |
| 2010/0201806 A1 | 8/2010 | Nygaard et al. |
| 2010/0245850 A1 | 9/2010 | Lee et al. |
| 2011/0005899 A1 | 1/2011 | Grzelak |
| 2011/0163517 A1* | 7/2011 | Groeneweg ............... B60P 3/00 280/423.1 |
| 2012/0105429 A1 | 5/2012 | Nygaard |
| 2012/0028575 A1 | 11/2012 | Turner |
| 2012/0293623 A1 | 11/2012 | Nygaard |
| 2012/0293789 A1 | 11/2012 | Nygaard |
| 2012/0303157 A1 | 11/2012 | Chung |
| 2013/0235371 A1 | 9/2013 | Nygaard et al. |
| 2013/0258046 A1 | 10/2013 | Nygaard |
| 2014/0043610 A1 | 2/2014 | Engel et al. |
| 2014/0063509 A1 | 3/2014 | Nygaard et al. |
| 2014/0168661 A1 | 6/2014 | Nygaard et al. |

FOREIGN PATENT DOCUMENTS

| | | |
|---|---|---|
| WO | 2005022076 A2 | 3/2005 |
| WO | 2009130062 A1 | 10/2009 |
| WO | 2015079335 A1 | 6/2015 |

OTHER PUBLICATIONS

Notice of Allowance and Fee(s) Due; related U.S. Appl. No. 14/876,192, dated Mar. 31, 2016.
International Preliminary Report on Patentability; Related International Application No. PCT/US2014/016390; dated Nov. 3, 2015.
Extended European Search Report, related European application No. 12786466.8; dated Feb. 16, 2015.
Notice of Allowance and Fee(s) Due; related U.S. Appl. No. 14/876,187, dated Mar. 14, 2016.
Extended European Search Report; related EP Application No. 13757558.5; date of completion of search Sep. 1, 2015.
<http://www.vision-systems.com/articles/2009/12/optics-amp-lenses-smart-optics-and-lenses-image-multiple-views.html>; retrieved on Apr. 19, 2016.
Screenshot dated Dec. 5, 2010.
Final Office Action; related U.S. Appl. No. 14/722,329; notification dated Nov. 18, 2016.
International Search Report and Written Opinion, International application No. PCT/US2015/016307; dated Jun. 3, 2015.
Brosed, Francisco Javier et al.; 3D Geometrical Inspection of Complex Geometry Parts Using a Novel Laser Triangulation Sensor and a Robot; Sensors 2011, 11, 9-110; doi:10.3390/s110100090; published Dec. 23, 2010.
Yogeswaran, Arjun; 3D Surface Analysis for the Automated Dtection of Deformations on Automotive Panels; Ottawa-Carleton Institute for Electrical and Computer Engineeeing School for Information Technology and Engineering, University of Ottawa; Apr. 2011.
International Search Report and Written Opinion; International application No. PCT/US14/16662; dated Dec. 8, 2014.
Notice of Allowance and Fee(s) Due; U.S. Appl. No. 14/221,410; dated Dec. 5, 2014.
International Search Report and Written Opinion, International application No. PCT/US2014/016663; dated May 28, 2014.
International Search Report and Written Opinion, International application No. PCT/US15/34349; dated Sep. 15, 2015.

* cited by examiner

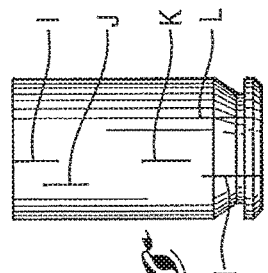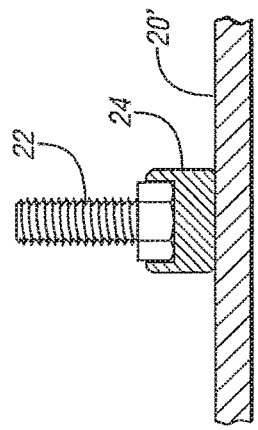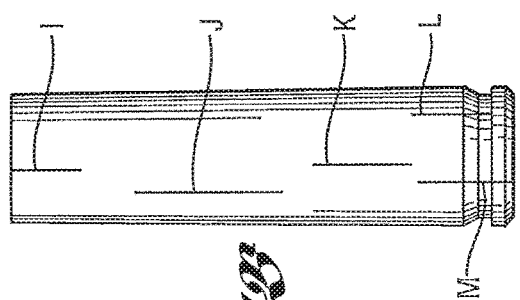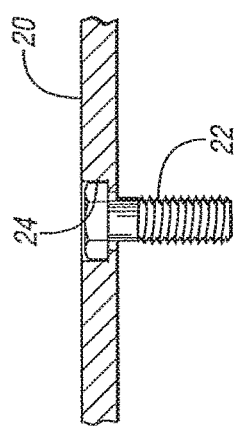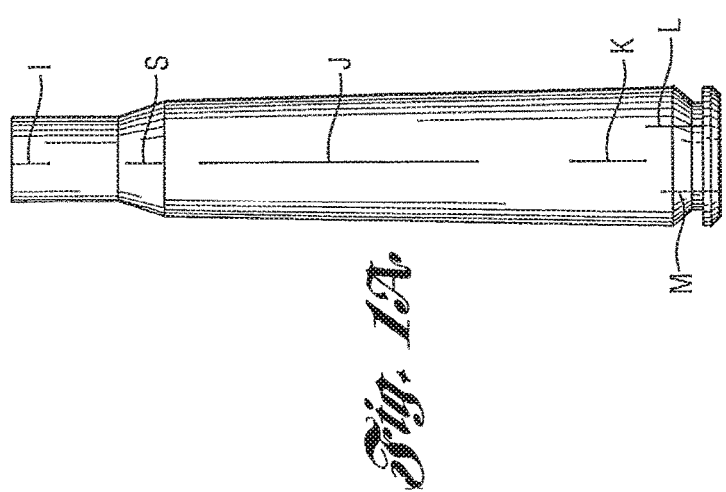

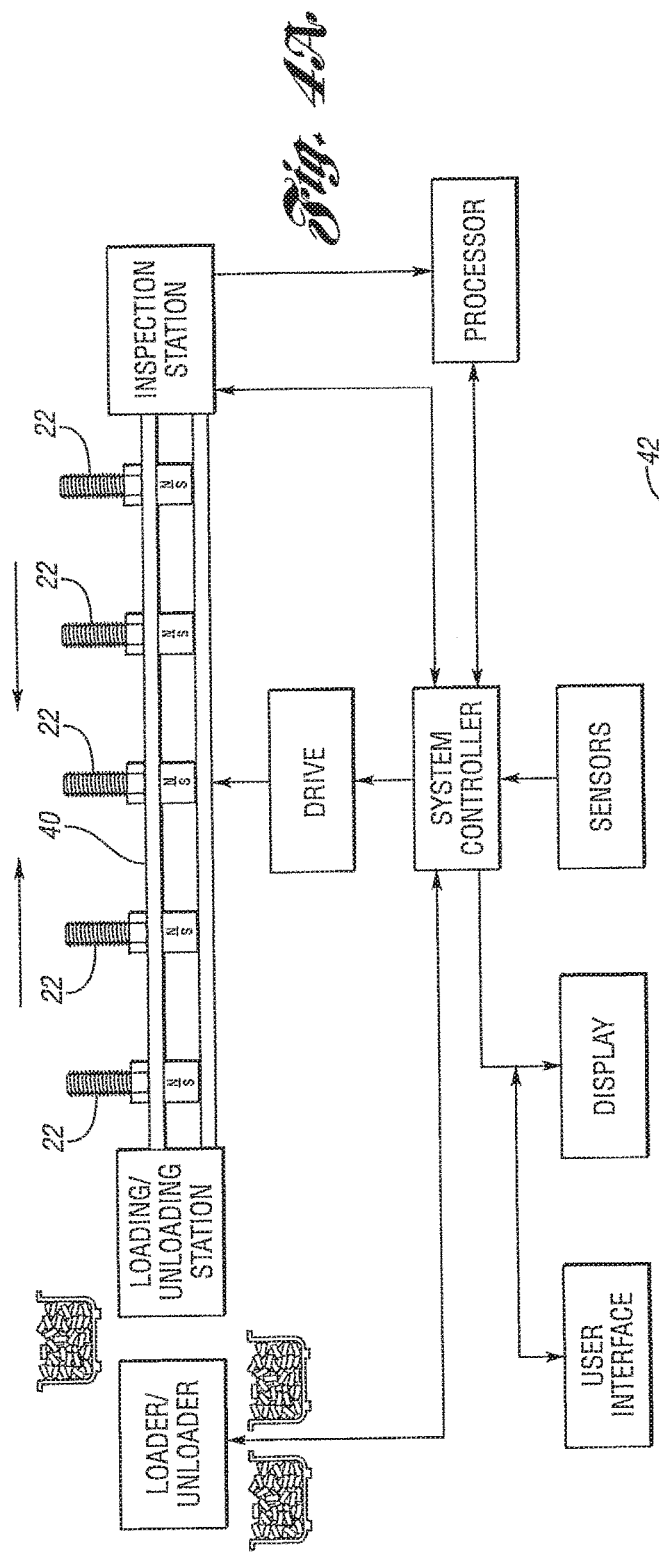
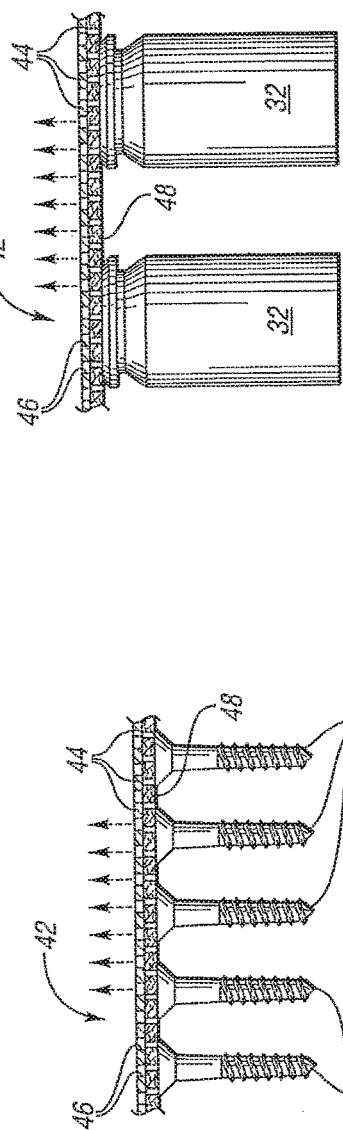

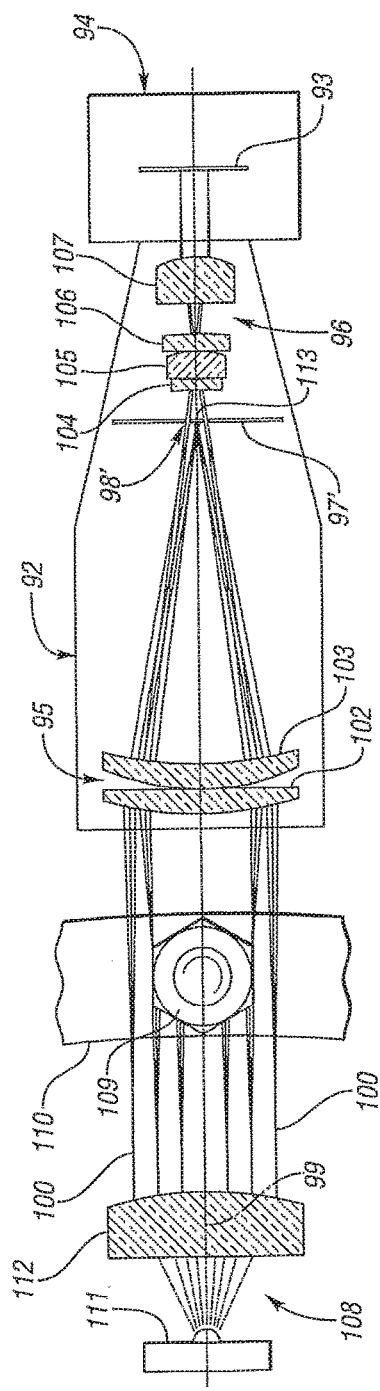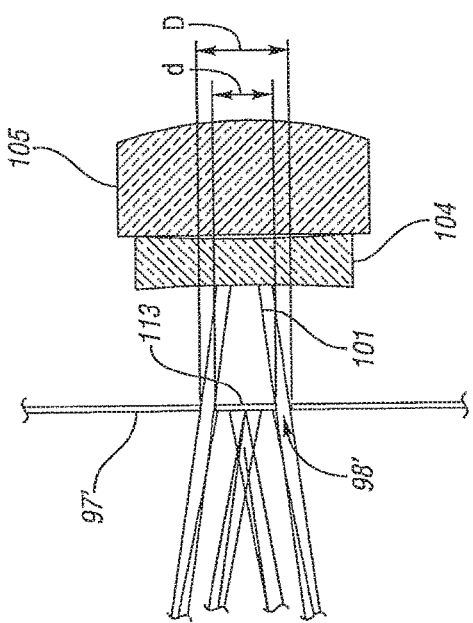

METHOD AND SYSTEM FOR OPTICALLY INSPECTING HEADED MANUFACTURED PARTS

CROSS-REFERENCE TO RELATED APPLICATIONS

This application is a continuation-in-part of U.S. patent application Ser. No. 15/501,033, filed Feb. 1, 2017, which is a national phase application of PCT/US2015/03439, filed Jun. 5, 2015, which claims priority to U.S. patent application Ser. No. 14/449,361, filed Aug. 1, 2014; a continuation-in-part of U.S. patent application Ser. No. 13/414,081, filed Mar. 7, 2012; a continuation-in-part of application Ser. No. 15/132,450, filed Apr. 19, 2016; which is a continuation-in-part of application Ser. No. 14/629,527, filed Feb. 24, 2015, now U.S. Pat. No. 9,575,013; which is a continuation-in-part of application Ser. No. 14/050,907, filed on Oct. 10, 2013, now U.S. Pat. No. 9,019,489; which is a continuation of application Ser. No. 13/109,369, filed on May 17, 2011, now U.S. Pat. No. 8,570,504; and is related to application Ser. No. 13/109,393, filed on May 17, 2011, now abandoned.

TECHNICAL FIELD

This invention relates in general to the field of the non-contact, optical inspection of headed manufactured parts and, more particularly, to methods and systems for optically inspecting parts, such as ammunition cases and threaded fasteners.

Overview

Traditional manual, gauging devices and techniques have been replaced to some extent by automatic inspection methods and systems. However, such automatic inspection methods and systems still have a number of shortcomings associated with them.

Inspection of defects on and in small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the U.S. Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

FIG. 1a is a side schematic view of a .50 caliber case. As explained in the above-noted military standard, a case is counted as a defective because of a split case if the cartridge case shows a definite separation of the metal entirely through the case wall. A case is classified as either a "major" or "critical" defect depending on the location of split. A split in the (I), (S) or (J) position is counted as a "major" defect when no loss of powder occurs; and as a "critical" defect when loss of powder occurs. A split in the (K), (L) or (M) position is counted as a "critical" defect.

FIG. 1b is a side schematic view of a .30 caliber case. As noted above, a case is counted as a defective because of a split case if the cartridge case shows a definite separation of the metal entirely through the case wall. A case is classified either as "major" or "critical" defective depending on location of split. A split in the (I) of (J) position is counted as a "major" defect when no loss of powder occurs; and as a "critical" defect when loss of powder occurs. A split in the (K), (L), or (M) position is counted as a "critical" defect.

FIG. 1c is a side schematic view of a .45 caliber case. Again, as noted above, a case is counted as defective because of a split case if the cartridge case shows a definite separation of the metal entirely through the case wall. A case is classified either as a "major" or "critical" defective depending on the location of the split. A split in the (I) or (J) position is counted as a "major" defect when no loss of powder occurs; and as a "critical" defect when loss of powder occurs. A split in the (K), (L), or (M) position is counted as a "critical" defect.

U.S. Pat. No. 4,923,066 discloses an automatic visual inspection system for small arms ammunition which sorts visual surface flaws at high speed according to established standards which can be tailored to fit specific needs.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact laser-based sensor guided by a precision mechanical system to scan a thread form producing a set of digitized images of the thread form.

WO 2009/130062 discloses a method and a device for the optical viewing of objects.

U.S. Pat. No. 4,547,674 discloses a method and apparatus for inspecting gear geometry via optical triangulation.

U.S. Pat. No. 4,970,401 discloses a non-contact triangulation probe system including a base plate and a first non-contact triangulation probe including a light source mounted on a first movable slide.

U.S. Pat. Nos. 5,168,458 and 5,170,306 disclose methods and systems for gauging threaded fasteners to obtain trilobular parameters.

U.S. Pat. No. 6,027,568 discloses an apparatus for processing fasteners in which the fasteners are conveyed for barrier coating by a split belt conveyor system having two continuous conveyor belts that provide a channel between the belts.

U.S. Pat. No. 6,787,724 discloses a sorting machine in which hex-headed bolts are received from a feed station onto a dual belt conveyor system, wherein the downward facing annular surface of the head of each bolt rests directly upon the dual belts as the bolt is transported within the sorting machine.

Other U.S. patents documents related to the invention include: U.S. Pat. Nos. 4,315,688; 4,598,998; 4,644,394; 4,852,983; 4,906,098; 5,521,707; 5,608,530; 5,646,724; 5,291,272; 6,055,329; 4,983,043; 3,924,953; 5,164,995; 4,721,388; 4,969,746; 5,012,117; 7,684,054; 7,403,872; 7,633,635; 7,312,607; 7,777,900; 7,633,046; 7,633,634; 7,738,121; 7,755,754; 7,738,088; 7,796,278; 7,684,054; and 7,812,970; and U.S. published patent applications 2010/0245850 and 2010/0201806.

SUMMARY OF EXAMPLE EMBODIMENTS

In one example embodiment, a method of optically inspecting parts is provided. Each of the parts has a length, a width, and an axis. The method includes supporting a part to be inspected at a loading station. The method also includes transferring the supported part so that the part travels along a first path which extends from the loading station to an inspection station at which the part has a predetermined position and orientation for inspection. The method further includes simultaneously illuminating a plurality of exterior side surfaces of the part which are angularly spaced apart about the axis of the part at the inspection station with a plurality of separate beams of radiation. Each of the illuminated side surfaces includes a pair of spaced apart lateral edges of the part. The method still further includes forming an optical image of at least a portion of each of the illuminated side surfaces of the part. The method including detecting the optical images and processing the detected optical images to obtain a plurality of views of the part which are angularly spaced about the axis of the part. The method further includes transferring the part after the inspection at the inspection station so that the inspected part travels along a second path which extends from the inspection station to an unloading station.

The views may be substantially equally spaced about the axis of the part at the inspection station.

The part may be stationary at the inspection station.

The loading station may be coincident with the unloading station.

The method may further include the step of coordinating the inspection of the part at the inspection station with the transfer of the part to and from the inspection station to control movement of the part and the inspecting of the part.

The first and second paths may define a loop-shaped path wherein each of the stations is located along the loop-shape path.

The detected images may be processed to identify a defective part.

The detected images may be processed to obtain a measurement of the part.

The method may further include displaying at least one view of the part.

The step of illuminating may include the step of generating a single beam of radiation and dividing or splitting the single beam of radiation into the separate beams of radiation.

The radiation may be visible light radiation or ultraviolet radiation.

Each of the separate beams of radiation may be a reflected beam of radiation.

The parts may include cartridge cases.

The detected optical images of the case may be processed to determine at least one of a dent, a split, a perforation, a crack, a scratch, a wrinkle, a buckle, a bulge, and a surface blemish located at the side surfaces of the case.

The parts may include threaded fasteners.

In another example embodiment, a system for optically inspecting parts is provided. Each of the parts has a length, width, and an axis. The system includes a part transfer subsystem including a transfer mechanism adapted to receive and support a part at a loading station and to transfer the supported part so that the part travels along a first path which extends from the loading station to an inspection station at which the part has a predetermined position and orientation for inspection and to transfer the part after inspection at the inspection station so that the inspected part travels along a second path which extends from the inspection station to an unloading station. The system further includes an illumination assembly to simultaneously illuminate a plurality of exterior side surfaces of the part which are angularly spaced apart the axis of the part with a plurality of separate beams of radiation when the part is located at the inspection station. Each of the illuminated side surfaces includes a pair of spaced apart lateral edges of the part. The system still further includes a telecentric lens and detector assembly to form an optical image of at least a portion of each of the illuminated side surfaces of the part and to detect the optical images. The system finally includes a processor to process the detected optical images to obtain a plurality of views of the part which are angularly spaced about the axis of the part.

The telecentric lens may include a forward set of optical elements having an optical axis and an aperture diaphragm. The diaphragm is provided with a transparent window substantially centered on the optical axis and located at a focal point along the optical axis of the forward set of optical elements.

The telecentric lens may further include a rear set of optical elements wherein the diaphragm is interposed between the forward set and the rear set with the transparent window located at the focal points of the forward and rear sets of optical elements.

The detector may include an image sensor having an image plane to detect the optical images.

The illumination assembly may include a single source of radiation and a mirror subassembly to receive and divide the radiation into the plurality of separate beams of radiation.

Parts may include cartridge cases such as non-magnetic (i.e., brass) ammo cartridges.

The detected optical images may be processed to determine at least one of a dent, a split, a perforation, a crack, a scratch, a wrinkle, a buckle, a bulge, and a surface blemish located at the side surfaces of the case.

The parts may include threaded fasteners, such as bolts and screws whether magnetic or non-magnetic (i.e., stainless steel or titanium).

The views may be substantial equally spaced about the axis of the part at the inspection station.

The transfer mechanism may include a conveyor such as a magnetic conveyor or a vacuum transfer conveyor.

The vacuum transfer conveyor may include a perforated conveyor belt wherein a head of the part is held against a surface of the belt.

The transfer mechanism may include a moveable table or disk or the transfer mechanism may be a vacuum transfer mechanism.

The transfer mechanism may include a split belt conveyor in which the head of the part is supported in a channel between the belts.

The transfer mechanism may include a split belt conveyor in which the part is suspended in a channel between the belts by engagement of its head with the belts.

The illumination assembly may include a partially reflective mirror interposed between the source and the mirror subassembly to allow the radiation to pass therethrough in a first direction and to prevent radiation from passing therethrough in a second direction opposite the first direction.

The source of radiation may include an LED emitter and an optical group to collimate rays of radiation emitted by the emitter.

The transparent window may be an annular window substantially centered on the optical axis. The optical images may include the illuminated pairs of lateral edges of the part.

The mirror subassembly may include at least one mirror disposed on one side of the first and second paths and at least one mirror disposed on the opposite side of the first and second paths.

The forward set of optical elements may receive rays of radiation having a narrow range of incident angles from the illuminated pairs of lateral edges. The received rays are substantially parallel to the optical axis.

In yet another embodiment, a system for optically inspecting parts is provided. Each of the parts has a head and a length, a width and an axis. The system includes a part transfer subsystem including a transfer mechanism adapted to receive and support a plurality of parts at their heads in spaced apart relationship at a loading station and to transfer the support parts so that the parts travels along a first path which extends from the loading station to an inspection station at which the parts have a predetermined position and orientation for inspection and to transfer the parts after inspection at the inspection station so that the inspected parts travel along a second path which extends from the inspection station to an unloading station. The system further includes an illumination assembly to simultaneously illuminate a plurality of exterior side surfaces of each part which are angularly spaced about the axis of the part with a plurality of separate beams of radiation when the part is located at the inspection station. Each of the side surfaces including a pair of spaced apart lateral edges of the part. The system still further includes a telecentric lens and detector assembly to form an optical image of at least a portion of each of the illuminated side surfaces and to detect the optical images. Finally, the system includes a processor to process the detected images to obtain a plurality of views of each of the parts angularly spaced about the axes of the parts.

The system may further include a system controller to control the part transfer subsystem and the illumination assembly to control the flow of parts and the inspecting of the parts at the inspection station.

In yet another embodiment a method of optically inspecting manufactured parts is provided. Each of the manufactured parts of the type having a length, a width, an axis and a head with an underside bearing surface. The method provides for complete 360° side, top and bottom high speed (i.e. 300 parts per minute) inspections of a stream of spaced parts at a single inspection station after which the stream of inspected parts is sorted based on the inspections. The method includes the step of feeding the part onto an angulated, split track configured as a pair of glide rails separated by a gap, to suspend the part on the rails by its underside bearing surface, the track having sufficient angulation to permit the part to glide on the rails to an inspection station by gravitational force. The method also includes the step of simultaneously imaging at the inspection station a plurality of exterior side surfaces of the part which are angularly spaced about the axis of the part to form an optical image of at least a portion of each of the imaged side surfaces of the part. The method further includes the step of detecting the optical images. The method further includes the step of processing the detected optical images to obtain a plurality of views of the part which are angularly spaced about the axis of the part. The method includes the still further step of routing the part after inspection to an unloading station.

In yet another embodiment a system for optically inspecting manufactured parts is provided. Each of the manufactured parts of the type having a length, a width, an axis and a head with an underside bearing surface. The system provides for complete 360° side, top and bottom high speed (i.e. 300 parts per minute) inspections of a stream of spaced parts at a single inspection station after which the stream of inspected parts is sorted based on the inspections. The system includes an angulated, split track configured as a pair of parallel glide rails separated by a channel, to suspend a part on the rails by its underside bearing surface, the track having sufficient angulation to permit the part to glide on the rails to an inspection station under gravitational force. The system also includes an imaging assembly at the inspection station to simultaneously image a plurality of exterior side surfaces of the part which are angularly spaced about the axis of the part when the part is located at the inspection station, the assembly including a detector assembly to simultaneously form an optical image of at least a portion of each of the imaged side surfaces of the part and to detect the optical images. The system further includes a processor to process the detected optical images to obtain a plurality of views of the part which are angularly spaced about the axis of the part.

The system may include glide rails having metal surfaces for contacting the underside bearing surface of the manufactured part head.

The glide rails may have stainless steel surfaces for contacting the underside bearing surface of the manufactured part head.

The surfaces of the glide rails contacting the underside bearing surface of the manufactured part head have a friction-reducing coating.

The surfaces of the glide rails contacting the underside bearing surface of the manufactured part head may have a friction-reducing coating of a boron-based formulation.

The glide rails may include material of sufficient transparency to permit viewing of the underside bearing surface at the inspection station.

The glide rails may be formed of parallel filamentary material.

The track may be mounted within a frame, and the angle of the track adjustable by a hinged connection to the frame.

One end of the track may have a fixed vertical position relative to the frame and the vertical position of the other end of the track be adjustable through a height-adjustment mechanism connected to the frame.

The processor capability may include performing a comparison of one or more of the plurality of views of the manufactured part to determine if a part parameter or property is within a range of acceptable values.

The channel dimension may adjustable by an adjustment mechanism for controlling the separation of the glide rails to accommodate parts of differing widths.

The system may further include a reject mechanism responsive to a signal from the processor for controlling the routing of conforming parts and non-conforming parts after each part exits the track.

The reject mechanism may comprise an air blow off device for selective routing of each part after it exits the track.

The system may further include an overhead camera for imaging the top surface of the part and providing the image to the processor to determine if the part head conforms to a predetermined parameter or property within a range of acceptable values.

The overhead camera may include a pericentric lens for viewing the top and side surfaces of the part head.

The channel dimension may be adjustable by a mechanism for controlling the separation of the glide rails to accommodate parts of differing widths, and the overhead camera is coupled to such mechanism through gears that move the overhead camera an amount proportionate to the adjustment of the channel dimension to keep the overhead camera properly positioned over the part in the inspection station.

The system may include an illumination source at the inspection station, and the channel dimension may be adjustable by a mechanism for controlling the separation of the glide rails to accommodate parts of differing widths, and the illumination source is coupled to such mechanism through gears that move the illumination source an amount proportionate to the adjustment of the channel dimension to properly position the illumination source relative to the part in the inspection station.

Other technical advantages will be apparent to one skilled in the art from the following figures, descriptions and claims. Moreover, while specific advantages have been enumerated, various embodiments may include all, some or none of the enumerated advantages.

BRIEF DESCRIPTION OF THE DRAWINGS

For a more complete understanding of the present invention, and for further features and advantages thereof, reference is made to the following description taken in conjunction with the accompanying drawings, in which:

FIG. 1a is a side schematic view of a .50 caliber cartridge case;

FIG. 1b is a side schematic view of a .30 caliber cartridge case;

FIG. 1c is a side schematic view of a .45 caliber cartridge case;

FIG. 2a is a side schematic view, partially broken away in cross section, of a threaded fastener received and retained in a transfer mechanism;

FIG. 2b is a side schematic view, partially broken away and in cross section, of a threaded fastener which head is received and retained within a chuck component or fixture which, in turn, is received and retained on a transfer mechanism;

FIG. 4a is a block diagram schematic view of another example of a system of the invention at inspection, loading and unloading stations;

FIG. 4b is a side view, partially broken away and in cross section, of a conveyor belt of a vacuum transfer conveyor wherein heads of parts such as screws are held against a bottom surface of a perforated belt;

FIG. 4c is a side view, partially broken away and in cross section, of a conveyor belt of a vacuum transfer conveyor wherein heads of parts such as cartridge cases are held against a bottom surface of the perforated belt;

FIG. 10b is similar to FIG. 10a with the threaded fastener at the inspection station with some radiation blocked by the threaded fastener and some radiation scattered by the edges of the threaded fastener and through a diaphragm of the telecentric lens;

FIG. 10c is an enlarged view, partially broken away, of a portion of the telecentric lens of FIG. 10b with corresponding rays of the radiation either blocked or passing therethrough the diaphragm;

DETAILED DESCRIPTION OF EXAMPLE EMBODIMENTS

FIG. 2a is a view of a transfer mechanism 20 for moving parts and from which a part such as a threaded fastener or bolt 22 hangs or is suspended from an aperture 24 in the transfer mechanism 20 at its head. In this way the threads of the bolt 22 are exposed for optical inspection by a system of at least one embodiment of the present invention. Other parts, such as the cases of FIGS. 1a-1c can be supported in a similar fashion.

FIG. 2b is a view of the threaded bolt 22 which is supported to stand on the upper surface of a transfer mechanism 20' by a chuck or fixture 24 mounted on the mechanism 20' at a fixed location thereon. The head of the bolt 22 is supported by and disposed within the fixture 24. This feature allows the threads of the bolt 22 to be optically inspected in another embodiment of a system of the present invention. Other parts, such as the cases of FIGS. 1a-1c can be supported in a similar fashion.

Generally, telecentric subsystems can extract optical edges and provide multiple side imaging of parts. One aspect of one embodiment of the present invention relates to a novel method and configuration which uses a telecentric subsystem including a telecentric or bi-telecentric lens to optically inspect parts which are received and supported on a transfer mechanism which moves the parts between loading, unloading, and inspection stations. At the inspection station the parts have a predetermined position and orientation for optical inspection.

Figure 3:
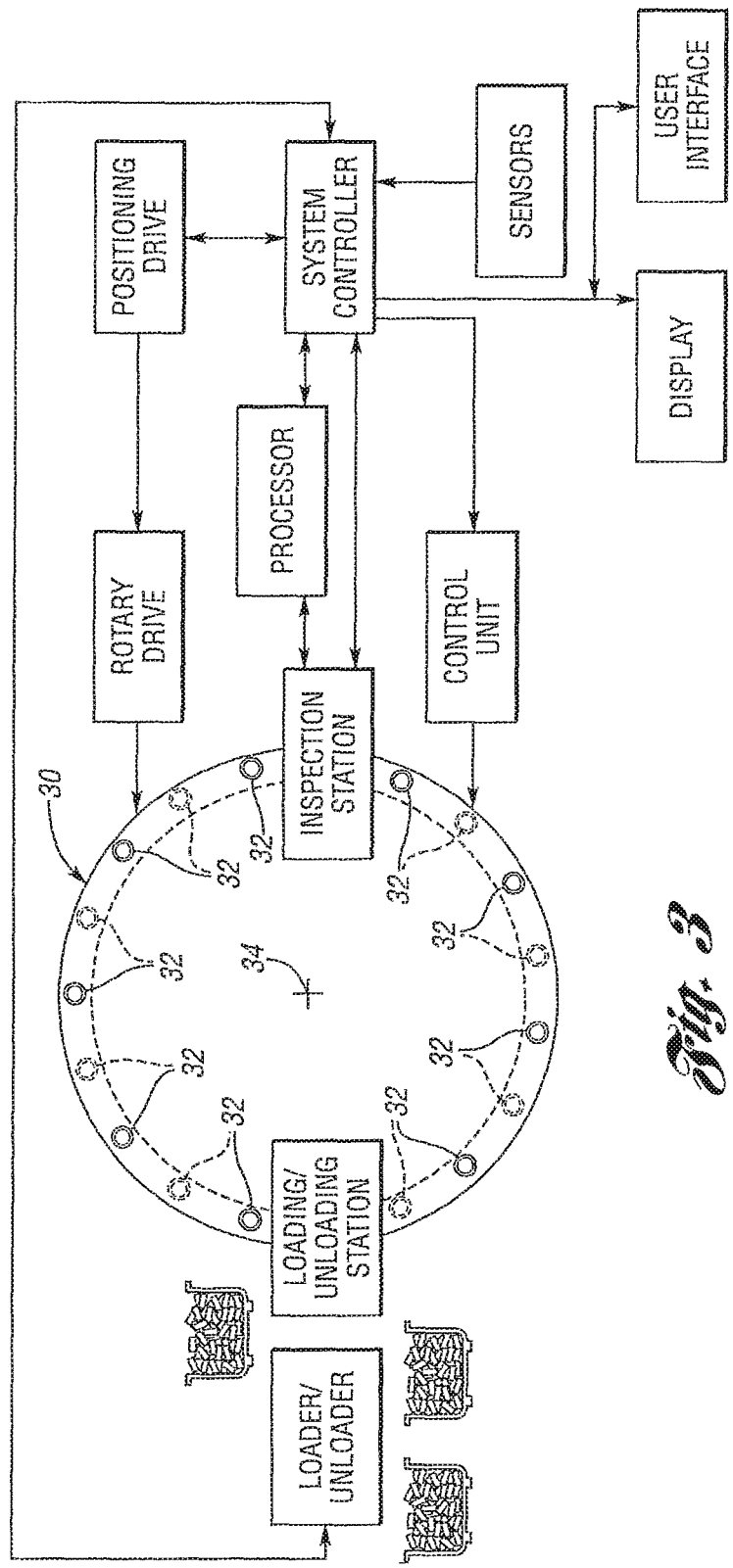
FIG. 3 is a block diagram schematic view of an example embodiment of a system of the invention at inspection, loading and unloading stations.

Referring now to FIGS. 3 and 4a, there are illustrated two different examples or embodiments of systems for optically inspecting parts such as ammunition cases or cartridges (FIG. 3) and threaded fasteners (FIG. 4a). Each of the systems of FIGS. 3 and 4 include, a part transfer subsystem including a transfer mechanism (30 in FIG. 3, 40 in FIG. 4a) adapted to receive and retain parts thereon at a loading station at which a loader loads parts to be inspected from a bin or other storage or transfer device. The transfer mechanism 30 or 40 then transfers the retained parts so that the parts travel along a first path which extends from the loading station to an inspection station at which the parts have a predetermined position and orientation for inspection. Subsequently, the transfer mechanism 30 or 40 transfers the parts after inspection at the inspection station so that the inspected parts travel along a second path which extends from the inspection station to an unloading station at which the inspected parts are unloaded from the transfer mechanism 30 or 40 by an unloader. The loader and unloader may be the same device, such as a robot having vision capabilities, which can place parts which "pass" the inspection in a "good part" bin and place parts which don't "pass" the inspection in a "defective part" bin. The unloading station may be coincident with the loading station and the loading and unloading may be done manually or automatically.

As illustrated in FIGS. 3 and 4a, the transfer mechanism 30 may be a rotating table or disk to transfer cases and the transfer mechanism 40 may include a conveyor such as a magnetic or vacuum conveyor for transferring parts such as threaded fasteners such as bolts 22 or screws. Magnetic conveyors are frequently used to convey ferromagnetic articles, such as cans, stampings and the like. In conveyors of this type, permanent magnets are located in the frame of the conveyor beneath the conveying run of an endless belt and articles are attracted to the magnets so that the belt can travel along an incline or vertical path of travel without the articles falling from the belt.

Alternatively, the transfer mechanism 30 can be modified to receive and retain threaded fasteners and the transfer mechanism 40 can be modified to receive and retain cartridge cases. The cartridge cases may be ferromagnetic or, if not ferromagnetic, magnets may be placed in the cases.

Alternatively, an indexing, beltless magnetic conveyor may be provided. Such a conveyer may include a housing defining a longitudinal length of the conveyor and a magnetic rack assembly moveably supported in the housing. The magnetic rack assembly includes a plurality of magnet assemblies supported at spaced intervals relative to one another along the longitudinal length of the conveyor. The beltless magnetic conveyor also includes a drive which is controlled by the system controller to index the magnetic rack assembly between a home or loading position proximate to one end of the housing and an end or inspection position which is proximate to an opposite end of the housing over the same path. The magnet assemblies are operable to generate a magnetic force which acts to attract ferromagnetic material toward the housing and to move the ferromagnetic material in the direction of the longitudinal length of the conveyor when the magnetic rack assembly is indexed.

Figure 6:
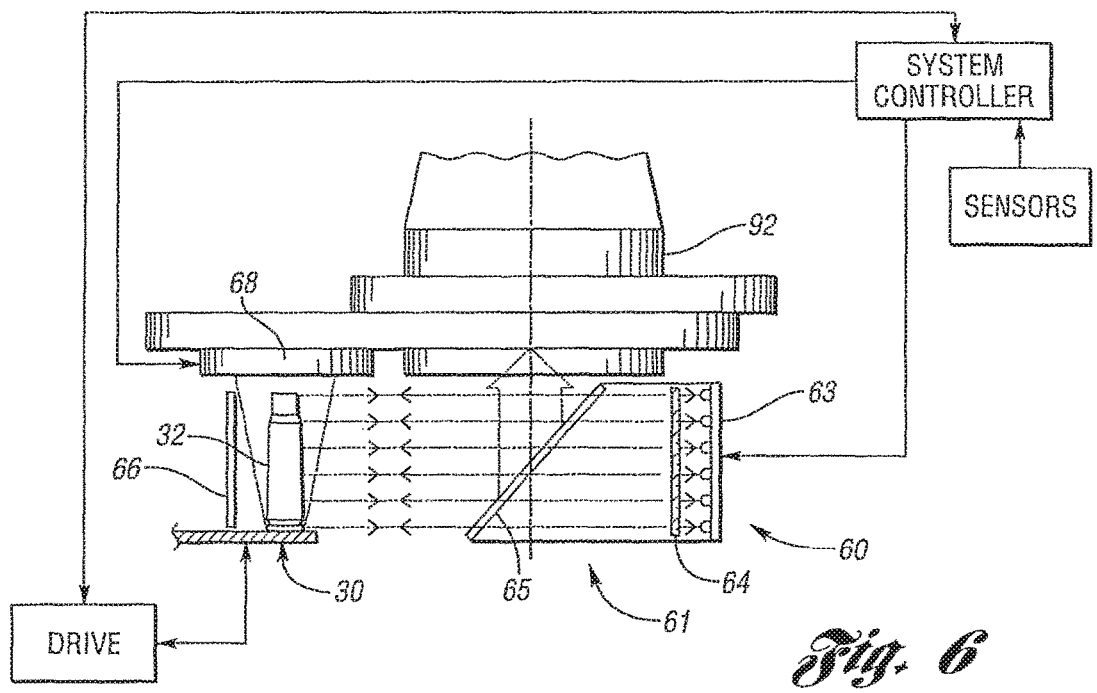
FIG. 6 is a side schematic block diagram view, partially broken away and in cross section, of two sources of illuminating radiation, a partially reflective mirror, the transfer mechanism of FIG. 5 and a telecentric lens and detector assembly associated with the mirror subassembly of FIG. 5.

As further illustrated in FIG. 3, the movable table or disk 30 may be a rotary index table or disk, for transferring parts such as ammunition cases or cartridges 32 either at the top or bottom surfaces of the table 30. The rotary index table 30 typically has a central rotational axis 34 and an outer periphery which has a round shape. A rotary drive of the table is illustrated in FIGS. 3 and 6 and operates to rotate the index table 30 on a base for indexing rotation about the rotational axis 34 based on various sensor input signals from sensors to a system controller which, in turn, provides sequential control signals to a positioning drive mechanically coupled to the rotary drive. The system controller also provides control signals to a computer display, a part loader/unloader (for example, a robot) and to a control unit which moves the rotary table 30 vertically in relation to its base so that the rotary drive can drive the index table 30 between stations. After the table 30 has moved to the desired station, the control unit controllably lowers the rotary table 30 back onto its base.

Also, alternatively, as illustrated in FIGS. 4b and 4c, the part transfer subsystem may include a vacuum transfer conveyor having a conveyor belt wherein parts, such as screws 32 (FIG. 4b) or cartridge cases 32 (FIG. 4c) are hung or held from their heads to enable lateral optical inspection of the parts. Such parts may include brass cartridge cases, stainless steel fasteners (such as screws) and titanium parts. Typically, such vacuum belt conveyors are capable of transferring small parts or articles between stations while maintaining a predetermined upright position of the part. Such conveyors or conveyor apparatus typically include a vacuum plenum 42, or mechanism for obtaining a vacuum in the plenum 42, a plurality of spaced air openings in a plenum wall 44 as well as an apertured vacuum transfer belt 48 having a reach mounted for movement along an outer surface of the plenum wall 44. The holes in the vacuum conveyor are spaced at intervals to provide a "metering effect" which allows the proper spacing for inspection and rejection of defective parts.

Figure 4D:
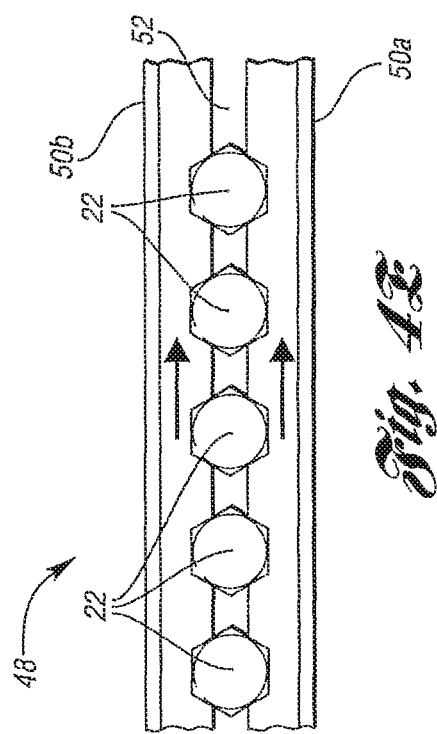
FIG. 4d is a side view, partially broken away and in cross section, of a split belt conveyor wherein parts such as hex-headed bolts are suspended from the channel between the belts and supported by a downward facing annular surface of the head of each bolt resting directly upon the belts.
Figure 4E:
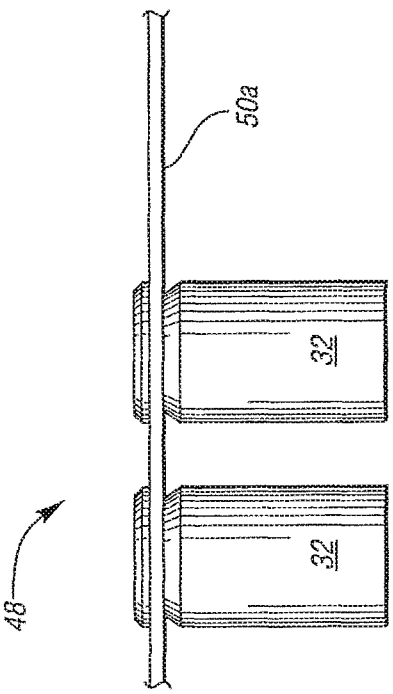
FIG. 4e is a plan view of the split belt conveyor of FIG. 4d.

A further alternative form of part transport system is illustrated in FIGS. 4d-4g, in which the parts are transferred by a split belt conveyor, indicated generally at 48. In FIGS. 4d and 4e, hex-headed bolts 22 are suspended by their heads in the channel 52 between the belts 50a and 50b. In this manner the shanks of the bolts 22 are exposed for inspection, less the portion of the portion of the shank just below the head occluded by the belts. The belts can be constructed of a number of different materials, provided that they exhibit high strength and engage the part securely to ensure the part is stable within the inspection station. A preferred material for the belts in the split belt conveyor of U.S. Pat. No. 6,027,568 is a stainless steel that is approximately 0.625" wide and approximately 0.032"-0.050" thick. As can readily be appreciated, belts having many different thicknesses and widths can also be utilized depending upon the shape of the particular part to be conveyed.

Figure 4F:
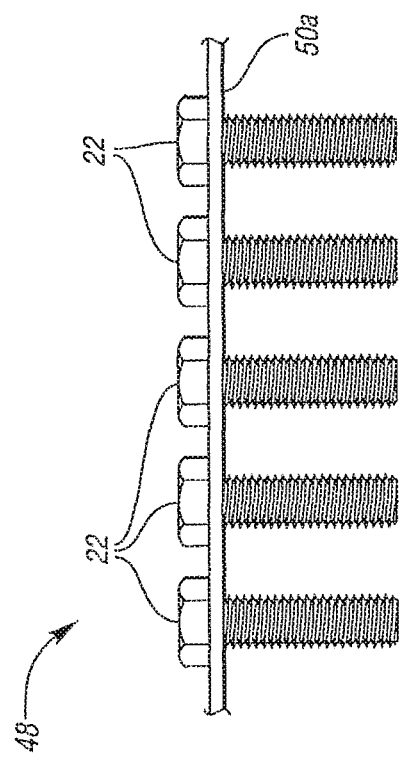
FIG. 4f is an alternative arrangement for transport of a part, such as bolt with a flanged head, on a split belt conveyor of the type illustrated in FIGS. 4d and 4e.

FIG. 4f is an alternative arrangement for transport of a part, such as bolt 22' with a flanged head, on a split belt conveyor 48 of the type illustrated in FIGS. 4d and 4e.

Figure 4G:
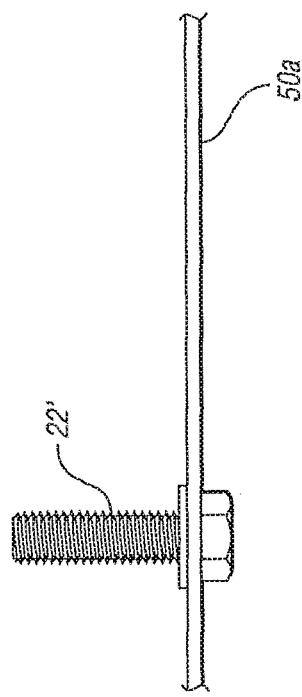
FIG. 4g is a side view, partially broken away and in cross section, of a split belt conveyor wherein parts such as cartridge cases are suspended from the channel between the belts and supported by a downward facing annular surface of the head of each case resting directly upon the belts.

FIG. 4g shows an adaptation of the split belt conveyor 48 to transport cartridge cases 32. The cartridge cases 32 are suspended from the channel 52 between the belts 50a and b, and supported by a downward facing annular surface of the head of each case resting directly upon the belts.

Figure 5:
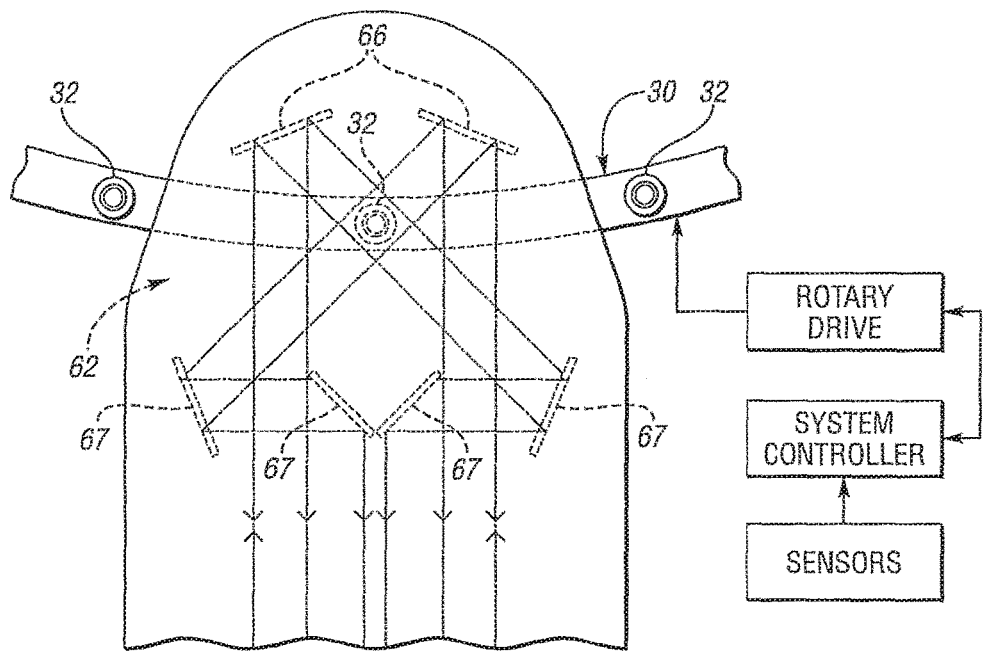
FIG. 5 is top schematic block diagram view, partially broken away, of a mirror subassembly (in phantom), a transfer mechanism for cartridge cases and a system controller of an embodiment of the invention.

Referring now to FIGS. 5 and 6, there is illustrated a first embodiment of an illumination assembly, generally indicated at 60, to simultaneously illuminate a plurality of exterior side surfaces of the part such as the cartridge cases 32 supported on the table 30. (The positioning drive has been omitted for purposes of brevity in the figures except for FIG. 3.) The side surfaces are angularly spaced about the axis of the case 32 and are illuminated with a plurality of separate beams of radiation when the case 32 is located at the inspection station. Each of the illuminated side surfaces including a pair of spaced apart lateral edges of the case 32.

The illumination assembly 60 includes a diffusive source 61 of radiation and a mirror subassembly, generally indicated at 62, to receive and divide the radiation into the plurality of separate beams of radiation as shown in FIG. 5. The source 61 of radiation includes an LED emitter 63 controlled by the system controller and at least one optical element 64 or diffuser to diffuse the rays of radiation emitted by the emitter 63. The emitter 63 includes a plurality of LED's. The illumination assembly 60 also includes a partially reflective mirror or beam splitter 65 interposed between the source 61 and the mirror subassembly 62 to allow the radiation to pass therethrough in a first direction and to prevent radiation from passing therethrough in a second direction opposite the first direction.

The beam splitter 65 is located within the optical path to direct light energy reflected back along the optical path from the cartridge cases 32 to a telecentric lens 92 and a detection device 94 (in FIG. 9) which typically includes a camera, which may be a digital CCD camera (e.g.; color or black/white) and an associated frame grabber (or digital frame buffer provided with the camera), which digitizes the video output from the television camera to obtain pixel data representing a two-dimensional image of portions of the side surfaces of the case 32. The pixel data are stored in a memory of the frame grabber, or transmitted, for instance, by a high speed link, directly to the processer of FIGS. 3 and 9.

The illumination assembly 60 may also include a ring LED illuminator 68 (FIG. 6) under control of the system controller to provide direct illumination of the case 32 and is used to enhance defects in the surface of the case 32.

The mirror subassembly 62 includes at least one mirror and preferably two mirrors 66 disposed on one side of the first and second paths which the cases 32 travel and at least one mirror and preferably four mirrors 67 disposed on the opposite side of the first and second paths as shown in FIG. 5.

The detected optical images are processed by the image processor to determine at least one of a dent, a split, a perforation, a crack, a scratch, a wrinkle, a buckle, a bulge, and a surface blemish located at the side surfaces of the case 32.

The system of FIGS. 5 and 6 (as well as the system of FIGS. 7 and 8) includes an integrated opto-mechanical subsystem designed to fully inspect and measure parts from their sides without any need for part rotation at the inspection station. The system of FIGS. 5 and 6 (as well as FIGS. 7 and 8) can inspect parts which are supported to stand upright (as shown in FIGS. 2b, 3, 4a and 5-8) or which can be suspended or supported from their heads (FIGS. 2a, 3, 4b and 4c).

Four orthonormal partially overlapped views of the part are simultaneously provided to the device 94 by the telecentric lens 92 through the array of mirrors 62. The optical path is designed so that the displacement angle between the views is almost exactly 90°. This optical layout ensures complete coverage of the case's lateral surfaces. The optical path is the same for all four viewpoints. Furthermore, telecentric imaging makes the system insensitive to case decentering and therefore suitable for measurement applications. The subsystem is the solution for inspecting parts, such as cases, whose features would be hidden when looked at from the top and for all those applications where a part must be inspected or measured from different sides without part rotation.

The illumination devices 60 and 68 are built into the subsystem to provide either backlight and/or direct part illumination, respectively.

Figure 7:
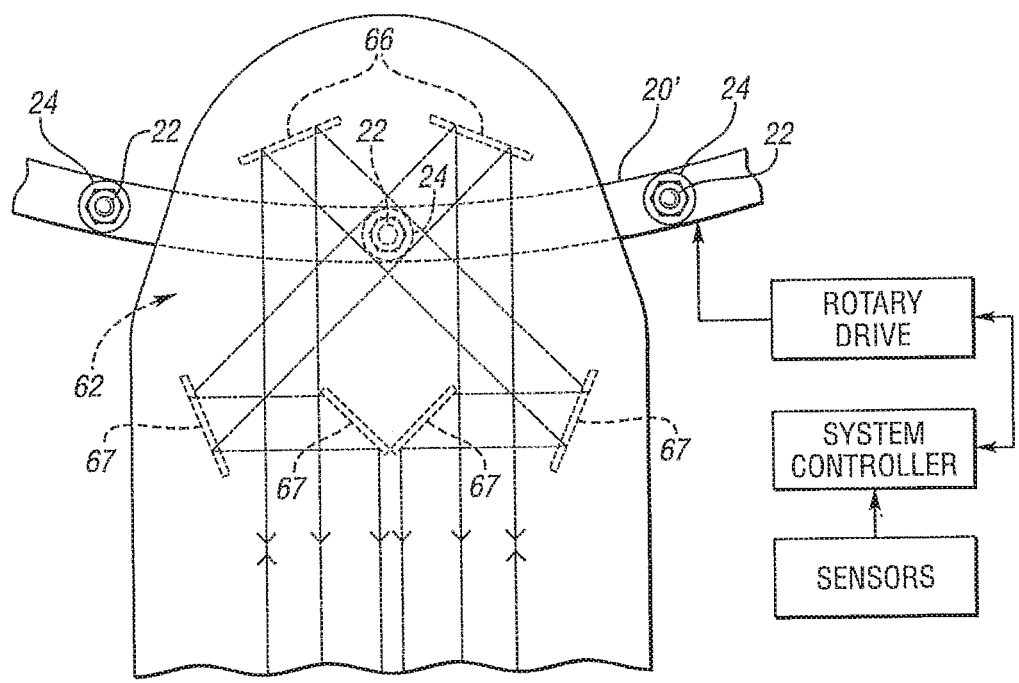
FIG. 7 is a top schematic block diagram view, partially broken away, of a mirror subassembly substantially identical to the mirror subassembly of FIG. 5, a transfer mechanism for threaded fasteners and a system controller.
Figure 8:
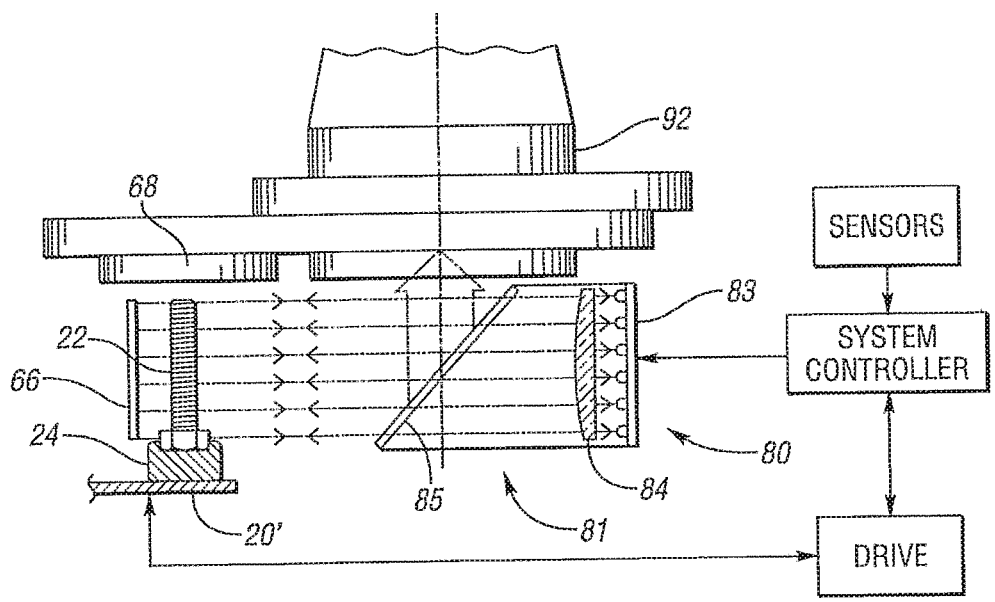
FIG. 8 is a side schematic block diagram view, partially broken away and in cross section, of a source of illuminating radiation, a partially reflective mirror, the transfer mechanism of FIG. 7 and a second embodiment of a telecentric lens and detector assembly corresponding to mirror subassembly of FIG. 7.

Referring now to FIGS. 7 and 8, FIGS. 7 and 8 correspond to FIGS. 5 and 6, respectively, except an illumination assembly, generally indicated at 80, includes a collimated source of radiation, generally included at 81, as well as the mirror subassembly 62. The collimated source 81 typically includes an LED emitter 83 and an optical group or set of lenses 84 to collimate the radiation emitted by the emitter 83. A beam splitter 85 is also provided and operates like the beam splitter 65 of FIG. 6. Also, the illuminator 68 may or may not be used. If used, the illuminator 68 would be controlled by the system controller.

The system also includes the telecentric lens 92 (with a slightly modified diaphragm) and a detector (such as the camera 94) to form an optical image of at least a threaded portion of each of the illuminated side surfaces of the threaded bolts 22 and to detect their optical images as described in detail herein.

Figure 9:
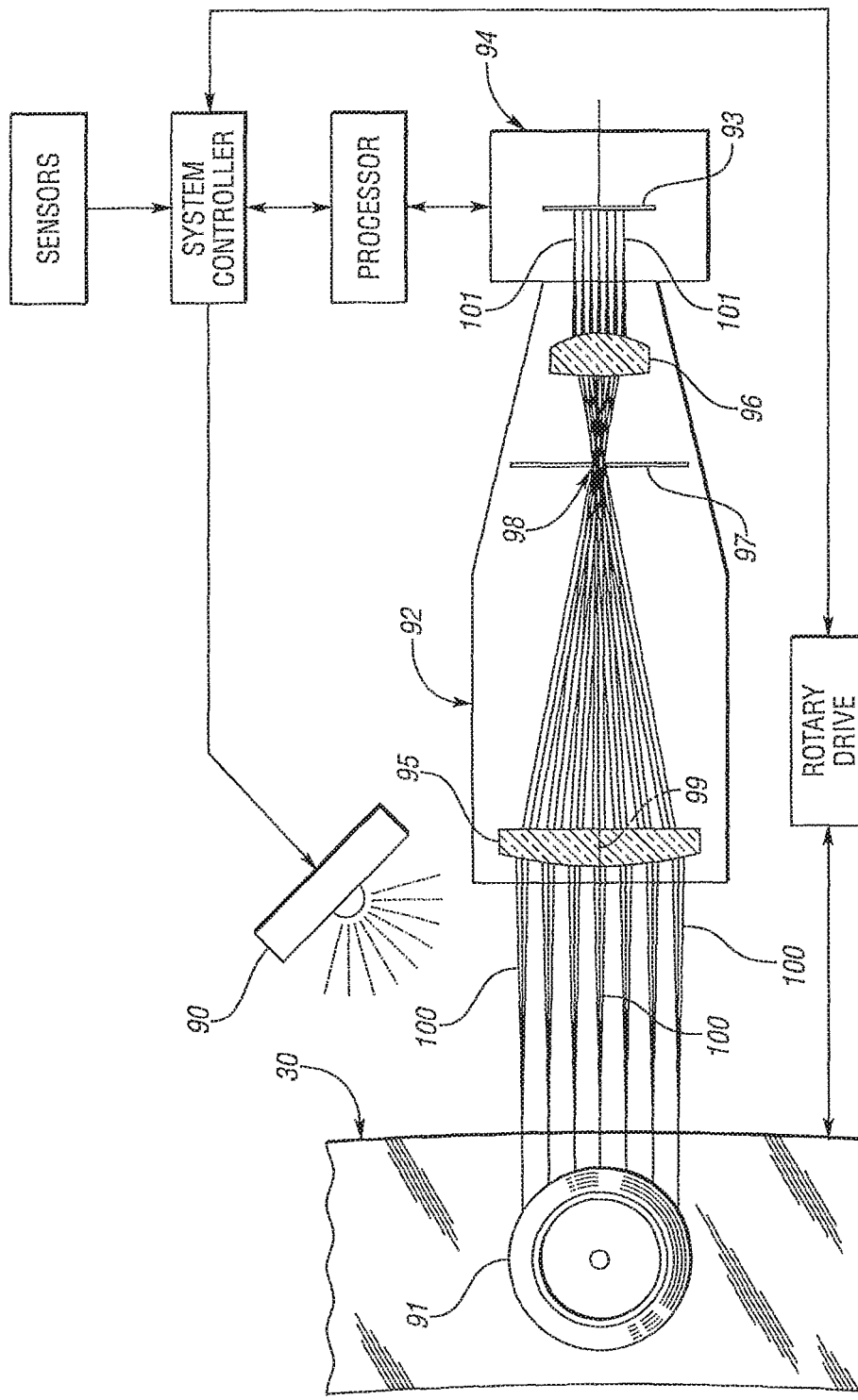
FIG. 9 is a top plan schematic block diagram view, partially broken away, of an illumination assembly, the telecentric lens and detector assembly of FIG. 6, the transfer mechanism of FIG. 6 and a system controller to obtain a view of one of the side surfaces of a cartridge case at an inspection station.

Referring to FIG. 9, there is illustrated an illumination assembly or radiant source 90 for illuminating an object such as an ammunition case to be imaged, and the telecentric optical lens 92 for receiving the reflected radiation from the case 91 and guiding it towards an image plane 93 of the image acquisition device or detector, generally referred as 94. The illumination assembly 90 is provided for illustrative purposes in FIG. 9, but it is to be understood that the preferred illumination assembly for the case 91 is illustrated in FIGS. 5 and 6. Consequently, the radiation source 90 preferably comprises a LED emitter including a plurality of LED emitter elements serving to emit radiation in either the visible or ultraviolet range. The LED emitter of the source 90 is preferably high power, capable of generating 100 optical mW or more for each emitting element. Also, the illumination assembly includes the mirror subassembly 62 wherein a plurality of side surfaces are illuminated and reflect light to the lens 92 for simultaneous imaging on the image plane 93.

Such as an optical or optoelectronic device for the acquisition of images (for example the camera or telecamera 94) has the image plane 93 which can be, for example, an electronic sensor (CCD, CMOS). The case 91 is received and retained at a predetermined position and orientation on a transfer mechanism such as the rotary table or disk 30. Preferably the device 94 is a high resolution digital telecamera, having the electronic sensor 93 with individual pixels of lateral dimensions equal to or less than one or more microns.

The lens 92 schematically comprises a forward set of optical elements 95 proximal to the case 91, a rear optical element 96 proximal to the acquisition device 94 and an aperture diaphragm 97 interpose between the forward set and the rear set of optical elements 95 and 96, respectfully. The aperture diaphragm 97 comprises a circular window 98 transparent to the radiation, which is referred to as a diaphragm aperture. For example, the aperture diaphragm 97 can comprise an opaque plate preferably of thickness of a few tenths of a millimeter, and the diaphragm aperture can be defined a simple hole in the plate.

The diaphragm aperture or window 98 is coaxial to the optical axis 99 of the forward set of optical elements 95, and positioned on the focal plane of the forward set 95 defined for the wavelength range of radiation emitted by the radiant source 90.

The position of the focal plane of a set of optical elements mostly depends on the refraction index of the material from which the lenses are made, which, in turn, depends on the wavelength of the electromagnetic radiation passing through the lenses.

The lens 92 only accepts ray cones 100 exhibiting a main (barycentric) axis that is parallel to the optical axis 99 of the forward set 95. Thereby, the lens 92 is a telecentric lens configured for the particular radiation. The rear set of optical element 96 serves to compensate and correct the residual chromatic dispersion generated by the forward set optical elements 95 for the wavelength in question.

The optical axis of the rear set 96 coincides with the optical axis 99 of the forward set 95 and the focal plane of the rear set 96 defined for the wavelength cited above, coincides with the plane on which the aperture diaphragm 97 is located. Consequently, rays of radiation 101 conveyed by the rear set 96 towards the image plane 93 form light cones, the main (barycentric) axis of which is parallel to the optical axis 99 of the lens 92.

Figure 10A:
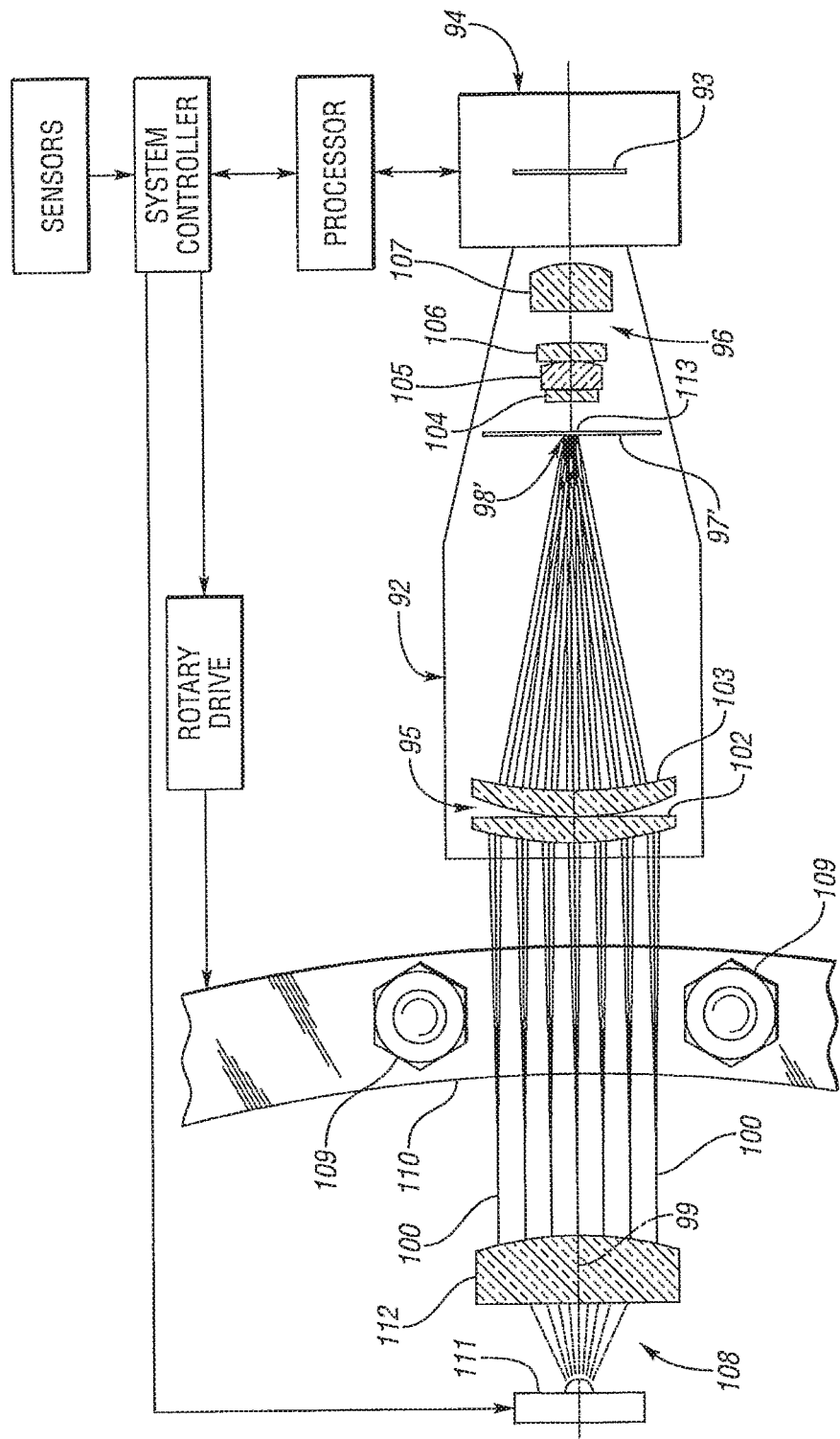
FIG. 10a is top plan schematic block diagram view, partially broken away, of the illumination assembly, the telecentric lens and detector assembly of FIG. 8, the transfer mechanism of FIG. 8 and a system controller to obtain a view of one of the side surfaces of a threaded fastener which is ready to index into the inspection station.

As illustrated in FIG. 10a, the forward set 95 preferably includes two positive lenses, 102 and 103, which can exhibit a flat-convex, bi-convex, or meniscus shape. The positive lenses 101 and 102 can both be made in common optical glass. For example, they can both be made in low chromatic dispersion crown glass, including, for example, Schott glass varieties classified with codes N-SK16, N-BK7, or B270.

As further illustrated in FIG. 10a, the rear set of optical elements preferably comprises four lenses respectively numbered from 104 to 107. The lens 104 which is proximal to a diaphragm 97' can be a negative lens serving to partially or completely correct the chromatic aberrations generated by the forward set 95. The negative lens 104 can be bi-concave, flat-concave, or meniscus shaped, and can be made of common optical glass, for example it can be made of high chromatic dispersion flint glass, for example Schott optical glass types classified with codes N-F2, LLF1, or N-SF1.

The rear lenses 105, 106 and 107 are positive lenses that can all be made in common optical glass, for example in low chromatic dispersion crown glass, including the hereinabove cited Schott optical glass types classified with codes N-SK16, N-BK7, or B270.

The lens 92 is therefore both telecentric on the object side and telecentric on the image side, and overall the lens 92 is a bi-telecentric lens configured for light such as visible light or ultraviolet light. It may be preferable that the lens 92 is optimized for operation with radiation in the ultraviolet range, such that the choice of materials from which the lenses are composed, and the characteristics of the lenses, including for example the curvature radius, thickness and spatial position, permit the lens 92 to operate in the above indicated wavelength range exhibiting very high contrast and with performance close to the diffraction limit.

Referring to FIG. 9, the aperture 98 may have a diameter of a few mm. In use, the object or case 91 is positioned in front of the bi-telecentric lens 92 where it is illuminated with radiation emitted by the radiant source 90. The radiation reflected by the case 91 passes through the bi-telecentric lens 92 and an image is formed on the sensor 93 of the telecamera or digital camera 94 for each side surface of the case which is illuminated.

The image obtained with the bi-telecentric lens 92 is an image substantially without errors of perspective and wherein the image size of the observed case 91 is independent of the distance from the case 91. The use of the bi-telecentric lens 92 with radiation in the preferred range also provides a high resolution image, exhibiting a level of detail of less than ten microns, compatible with the maximum resolution of the electronic sensor 93 of the telecamera 94.

The lens 92 used in the wavelength range is therefore particularly suited for use with devices 94 capable of high resolution image acquisition, wherein the individual image point (pixel) is very small, and wherein the density of these pixels is very high, thereby enabling acquisition of highly detailed images.

An image acquired in this way will comprise a high numbers of pixels, each of which contains a significant geometric datum based the high performance of the lens 92 operating in the wavelength range, thereby being particularly useful for assessing the dimensions of the object viewed by the lens 92. The high level of detail provided by the individual pixels of the device 94 enables, after suitable processing of the image an accurate determination of the outline of the object to be made, improving the efficiency of "edge detection" algorithms, these being algorithms of calculation normally used in the artificial viewing sector in order to select, from a set of pixels making up an image, those pixels that define the border of the objects depicted, and thereby to establish the spatial positioning and the size of the objects.

Consequently, the assembly of FIG. 9 offers a significant improvement in the accuracy of images in any type of application based on artificial viewing, in particular in the field of optical metrology, this being dimensional measuring, without contact, of objects, for example mechanical components including threaded fasteners such as screws and bolts as well as the cartridge cases 91.

FIGS. 10a and 10b illustrate another embodiment of the system which differs from the previously described system of FIG. 9 with respect to the radiant source and the diaphragm 97'. In the embodiment of FIGS. 10a and 10b a radiant source, generally indicated at 108, is provided for radiating collimated rays of radiation at parts such as a threaded bolt 109 received and retained on a transfer mechanism 110 such as a rotary table or disk 110 similar to the tables or disks 20 and 20'. Preferably, the radiant source 108 comprises an LED emitter 111 generally of the type previously described, and a set of optical components 112 that collimates the radiation emitted by the LED emitter 111 such that the transmitted rays are almost completely parallel. The radiant source 108 is located facing the bi-telecentric lens 92 and oriented such that the collimated rays leaving the optical group 112 are parallel to the optical axis 99 of the lens 92. However, it is to be understood that the radiant source 108 is provided for illustrative purposes but it is to be understood that the preferred illumination assembly 80 for the bolts 109 is illustrated in FIGS. 7 and 8 in the form of the mirror subassembly 62 and the collimated source 81 of radiation.

In this way, all the rays emitted by the LED emitter 111 and collimated by the optical group or set of lenses 112 are collected by the bi-telecentric optical lens 92, and projected onto the image plane 93 of the camera device 94, thereby supplying the camera device 94 with high levels of radiation per surface area. This characteristic makes the assembly efficient from the point of view of consumption of energy, as it provides images with a very high signal/noise ratio, notwithstanding the low spectral transmittance of light provided by common optical glass, from which the lenses of the forward set 95 and rear set 96 of the bi-telecentric lens 92 are made.

FIGS. 10a, 10b and 10c illustrate the acquisition by optical means of images only of the outlines of the threaded bolt 109 being backlit and viewed by separate beams obtained from a single source of radiation. In this embodiment the aperture diaphragm 97' preferably comprises a circular window 98' transparent to the emitted radiation, the window 98' being coaxial with the optical axis 99 of the forward set 95 and the rear set 96, and being located on the focal plane of both. In the center of the circular window 92 the diaphragm 97' comprises a disk-shaped opaque zone 113 (best shown in FIG. 10c) exhibiting a diameter smaller than the diameter of the circular window 98' thereby leaving an annular transparent opening centered on the optical axis 99 of the forward set 95 and the rear set 96 and defining the diaphragm aperture. Since the annular aperture of the diaphragm 97' lies on the focal plane of the forward set 95, with the opaque zone 112 intercepting the optical axis 99, the collimated rays from the radiant source 108 are focused by the forward set 95 at a point in proximity to the center of the opaque zone 113 as shown in FIG. 10a. The opaque zone 113 prevents the passage of radiation, and consequently none of the collimated rays generated by the radiant source 108 can reach the image plane 93 which remains completely masked with no bolts being illuminated.

The rays emitted by the radiant source 108 are never perfectly parallel to each other. Consequently, the minimum diameter d of the opaque zone 112 is expressed by the equation: $d = 2 \cdot F1 \cdot \alpha$ where $\alpha$ is the maximum angle of divergence of the luminous rays emitted by the radiant source 108, expressed in radians, and F1 is the focal length of the forward set 95 of the bi-telecentric lens 92. When there are no objects interposed between the radiant source 108 and the bi-telecentric lens 92 (as shown in FIG. 10a) the rays are intercepted or blocked by the opaque central part 113 of the diaphragm 97'. When an object such as the bolt 109 is interposed between the radiant source 108 and the bi-telecentric lens 92 as shown in FIG. 10b, the collimated rays 100 from the radiant source 108 that reach the object bolt 109 from behind are reflected back or absorbed, while those that interact with the edges of the bolt 109 are partly scattered in all directions in the surrounding space, resulting in the forward set 95 of the bi-telecentric lens 92 receiving light rays from various directions. The telecentric lens 92 in general only accepts light rays that are substantially parallel to the optical axis 99, when the inclination a of the rays 100 relative to the optical axis 99 does not exceed a limit value defined as a function of the diameter D of the transparent window 98' of the diaphragm 97' (FIG. 10c).

Of these almost or near parallel rays, those that are perfect parallel with the optical axis 99 or that have an inclination very close to parallel to the optical axis 99 are blocked by the opaque zone 113 of the diaphragm 97'. Consequently the annular transparent zone of the aperture diaphragm 97' permits passage only of the rays that reach the forward set 95 with an inclination relative to the optical axis 99, sufficiently small to pass through the annular transparent window 98' and simultaneous sufficiently large not to be focused on the opaque central zone 113. Typically, the annular transparent zone or window 98' of the aperture diaphragm 97' permits the passage only of light rays for which the following relations are simultaneously valid:

$$\alpha < \frac{D}{2*F1} \text{ and } \alpha > \frac{d}{2*F1}$$

where α is the inclination of the luminous ray relative to the optical axis 99 of the lens 92, F1 is the focal length of the forward set 95, D is the diameter of the circular window 98' and d is the diameter of the opaque central zone 112 (FIG. 10c). In these conditions the only light rays capable of reaching the image plane 93 and, consequently, forming an image are those originating by scattering from the edges of the threaded bolt (i.e. the threads) illuminated by the source 108 of collimated radiation.

Therefore, the assembly of FIGS. 10a, 10b, and 10c makes it possible to optically obtain images of the outlines or contours of the threaded bolt 109. From the above explanation, the same result could be obtained if the lens 92 comprised a simple object-side telecentric lens, on the condition that the diaphragm 97' exhibits a diaphragm aperture in the form of an annular-shaped transparent window as described above. The lens 92 may be configured to operate with ultraviolet or visible light on the condition that the diaphragm 97' of the lens 92 is located on the focal plane of the forward set 95 defined for the wavelength of the radiation.

In view of the above, the following are important considerations in the design of the illumination and telecentric and detector assemblies:

Standard telecentric lenses operate in the visible range;

In order to use an ultraviolet (UV) illuminator, it would be necessary to replace both the LED illuminator and the telecentric (TC) lens with the equivalent UV structures.

UV telecentric setups offer more contrast information at higher spatial frequencies compared to lenses operating in the visible range.

UV telecentric setups offer more contrast information at higher spatial frequencies compared to lenses operating in the visible range.

Telecentric lenses that are telecentric only in object space accept incoming rays that are parallel to the main optical axis. However, when those rays exit the optical system, they are not parallel anymore and would strike the detector at different angles. This results in:

lower constancy in magnification point spread function inhomogeneity (spots in image space would change in size depending on the position on the detector plane)

In bi-telecentric lenses, the optical rays remain parallel on in image space. That means increased constancy in magnification, more consistent information over the entire detector plane, superior depth of field.

Data/Image Processor for the Detection of Surface Defects on Small Manufactured Parts This vision system is especially designed for the inspection of relatively small manufactured parts such as threaded fasteners and small and medium caliber ammunition. The processing of images of the cartridge cases to detect defective cases is generally described in issued U.S. Pat. No. 7,403,872 as follows.

Dent Detection

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this theory. One option is to orient the light source so that light reflected off the part exterior is aimed directly into the camera aperture. Light which reflects off a dented region will not reflect bright background. Alternatively, the light source can be positioned with a shallower angle to the part. This will result in a low background illumination level with dents appearing as well deemed origin spots on the image.

The vision system detects dents on parts with multiple tapered sections. In particular, a bright background is created in highly tapered regions (with dents appearing as dark spots) while a dim background is created in flatter regions (with dents appearing as bright spots).

As previously mentioned, the vision system has two types of lights, each of which can be independently adjusted in order to properly illuminate a given taper.

Perforation Detection

Detecting perforations uses both of the principles outlined above. The task is much simpler however, as the region containing the defect is completely non-reflective. Therefore, perforations are visible as dark spots on surfaces illuminated by either shallow or steep angle illumination.

Software

Because the part is essentially at a pre-defined location and orientation when the images are acquired, the software need not auto-locate the part and identify regions of interest using preset visual clues.

Defect detection in each region of interest is typically conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Part Location

Previously locating the part in the image may be accomplished by running a series of linear edge detection algorithms. This algorithm uses variable threshold, smoothing and size settings to determine the boundary between a light and dark region along a defined line. These three variables are not generally available to the user, but are hard-coded into the software, as the only time they will generally need to change is in the event of large scale lighting adjustments.

The software first uses the above edge detection algorithm to find the back (left) end of the part in the image.

Once the left edge of the part has been located, the software runs four more edge searches along the top and bottom edges of the part.

Once the top and bottom edges of the part have been located, the midpoints of the edge pairs are calculated and joined in order to find the centerline.

The centerline search is then performed again, but rather than conducting the linear edge detections in the vertical direction, they are conducted perpendicular to the newly found centerline. This iteration reduces the small angle error associated with any potential misalignment of the part in the field of view.

A new centerline found using the results of the repeated top and bottom edge search.

Finally, the left edge is again located, this time along the new centerline. This action locates the very center of the left-hand edge of the part.

Part Regions

Figure 11:
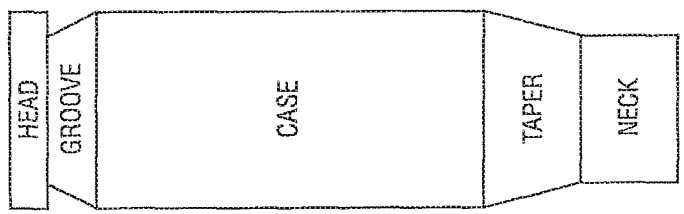
FIG. 11 is a schematic view wherein a framework in the figure is applied to a part such as a cartridge case once it has been located.

Once the part has been located in the image, a framework of part regions is defined using a hard-coded model of the anticipated part shape. In the case of ammunition, the regions defined by the framework include head, extractor groove, case, taper, and neck. Each of these regions can be varied in length and width through the user interface in order to adapt the software to varying case sizes. Note that although regions can be adjusted in size, they cannot have their bulk shape changed. A checkbox allows the taper and neck regions to be removed in order to inspect pistol cases (which do not have a taper). The size of the region framework as well as the state of the Taper/No-Taper checkbox is saved in the part profile. FIG. 11 shows the definition of the various regions on the part.

Figure 12:
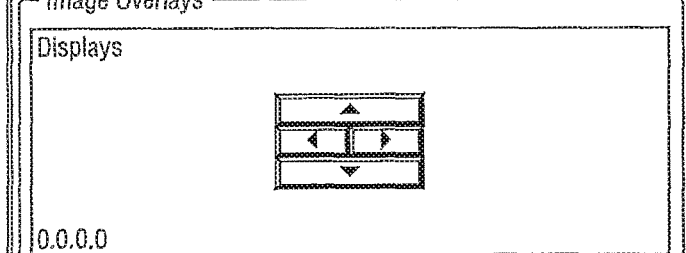
FIG. 12 is a schematic view of a screen shot which describes a cartridge case or bullet to be inspection.

This region definition is shown in screenshot of FIG. 12. Note how the diameter of the groove has been set to be the same as the diameter of the case, resulting in a rectangular groove profile, rather than the trapezoid that is more frequently used.

Defect Search

Figure 13:
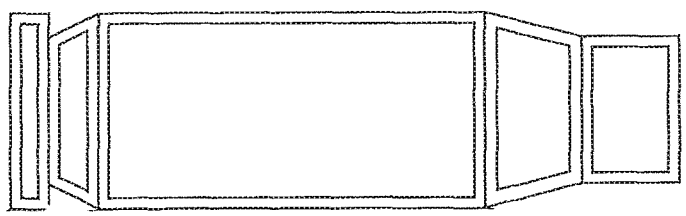
FIG. 13 is a schematic view similar to the view of FIG. 11 wherein buffers are applied once the case regions has been identified.

Once the case regions have been defined, a buffer distance is applied to the inside edges of each region. These buffered regions define the area within which the defect searches will be conducted. By buffering the inspection regions, edge anomalies and non-ideal lighting frequently found near the boundaries are ignored. The size of the buffers can be independently adjusted for each region as part of the standard user interface and is saved in the part profile. This concept is demonstrated in FIG. 13.

There are two general defect detection algorithms that can be conducted in each region. These two algorithms are closely tied to the detection of dents and perforations respectively as discussed above in the lighting section. More generally however, they correspond to the recognition of a group of dark pixels on a bright background or a group of bright pixels on a dark background.

Although there are only two defect detection algorithms used across all the regions on the part, the parameters associated with the algorithm can be modified from region to region. Additionally, the detection of dark and/or bright defects can be disabled for specific regions. This information is saved in the part profile.

Dark Defects

The detection of dark defects is a 6 step process.

1. Logarithm: Each, pixel brightness value (0-255) is replaced with the log of its brightness value. This serves to expand the brightness values of darker regions while compressing the values of brighter regions, thereby making it easier to find dark defects on a dim background.

2. Sobel Magnitude Operator: The Sobel Operator is the derivative of the image. Therefore, the Sobel Magnitude is shown below:

$$S_M = \sqrt{\left(\frac{\partial f}{\partial x}\right)^2 + \left(\frac{\partial f}{\partial y}\right)^2}$$

although it is frequently approximated as the following:

$$S_M = \frac{\frac{\partial f}{\partial x} + \frac{\partial f}{\partial y}}{2}$$

The Sobel Magnitude Operator highlights pixels according to the difference between their brightness and the brightness of their neighbors. Since this operator is performed after the Logarithm filter applied in step 1, the resulting image will emphasize dark pockets on an otherwise dim background. After the Sobel Magnitude Operator is applied, the image will contain a number of bright 'rings' around the identified dark defects.

3. Invert Original Image: The original image captured by the camera is inverted so that bright pixels appear dark and dark pixels appear bright. This results in an image with dark defect areas appearing as bright spots.

4. Multiplication: the image obtained after step 2 is multiplied with the image obtained after step 3. Multiplication of two images like this is functionally equivalent to performing an AND operation on them. Only pixels which appear bright in the resultant image. In this case, the multiplication of these two images will result in the highlighting of the rings found in step two, but only if these rings surround a dark spot.

5. Threshold: All pixels with a brightness below a specified value are set to OFF while all pixels greater than or equal to the specified value are set to ON.

6. Fill in Holes: The image obtained after the completion of steps 1-5 appears as a series of ON-pixel rings. The final step is to fill in all enclosed contours with ON pixels.

After completing these steps, the resultant image should consist of a pixels corresponding to potential defects. These bright blobs are superimposed on areas that originally contained dark defects.

Bright Defects

The detection of bright defects is a two-step process.

1. Threshold: A pixel brightness threshold filter may be applied to pick out all saturated pixels (greyscale255). A user-definable threshold may be provided so values lower than 255 can be detected.

2. Count Filter: A count filter is a technique for filtering small pixel noise. A size parameter is set (2, 3, 4, etc) and a square box is constructed whose sides are this number of pixels in length. Therefore, if the size parameter is set to 3, the box will be 3 pixels by 3 pixels. This box is then centered on every pixel picked out by the threshold filter applied in step 1. The filter then counts the number of additional pixels contained within the box which have been flagged by the threshold filter and verifies that there is at least one other saturated pixel present. Any pixel which fails this test has its brightness set to 0. The effect of this filter operation is to blank out isolated noise pixels.

Once these two steps have been completed, the resultant binary image will consist of ON pixels corresponding to potential defects. Furthermore, any "speckling" type noise in the original image which would have results in an ON pixel will have been eliminated leaving only those pixels which are in close proximity to other pixels which are ON.

Pixel Count

After bright and/or dark defect detection algorithms have been run in a given region, the resultant processed images are binary. These two images are then OR'ed together. This results in a single image with both bright and dark defects.

The software now counts the number of ON pixels in each detected defect. Finally, the part will be flagged as defective if either the quantity of defect pixels within a given connected region is above a user-defined threshold, or if the total quantity of defect pixels across the entire part is above a user-defined threshold.

Thread Signal/Data Processing

Introduction

What follows is a description of a thread parameter estimation process. This process which is described in general in published U.S. patent application 2010/0238435 provides one embodiment of a standard thread measurement "feature" in the method and system of the invention.

Thread Signal Processing

Thread signal processing is the process of estimating the following thread parameters.
 1) pitch
 2) major diameter
 3) minor diameter
 4) functional diameter
 5) lead deviation
 6) pitch diameter As the thread signal processing proceeds, a number of intermediate data products are produced in early processing stages that are further analyzed in later stages. These include:
 rough pos/neg crossing locations
 rough crest locations
 wire position search intervals
 left/right flank lines
 wire positions
 precise crest/root locations
 3-crest average/median measurements of major diameter, minor diameter, pitch diameter
 3-D crest cylinder axis
 wire position projections on the 3-D crest cylinder axis
 3-D crest cylinder diameter
 3-D crest root-mean-square distance between crest data and fit.

These intermediate data products are analyzed to produce final estimates of the thread parameters. For example major diameter is estimated as twice the radius of the 3-D crest cylinder. The 3-D crest cylinder axis then depends on the precise crest/root locations. The crest/root locations then depend on the search intervals based on rough crest locations and pos/neg crossings, and on data from the original calibrated part data.

Processing Restrictions

Inspection Region

The thread processing occurs between position limits called an inspection region. In template editor, the user specifies the inspection region by manipulating the upper and lower stage position limits, overlaid on an image of the part.

These limits utilize the calibrated sensor position so that measurements by are aligned to the approximately similar physical positions on the part.

The estimation of thread parameters is specified to be an average estimate over all the data within which the inspection region. In practice, some of the intermediate data products are estimated outside of the inspection region in order to allow estimation of all thread parameters within the full region. For example, a wire position within the inspection region may require a thread crest outside the inspection region.

Measurement Assumption for the Inspection Region

The following requirements guide the user's placement of the inspection region on the image of the part.

The first assumption is that the thread parameters be constant throughout the inspection region. This enables the software to average the estimates from different positions within the inspection region and not be concerned with partitioning or segmenting the data into different regions for special processing.

This requirement excludes the following types of data from the inspection region:
 the beginning or end of a threaded region, with thread crests less than full height.
 a threaded region with a taper.
 a threaded region with a notch or extensive damage.

A second assumption is that the inspection region contains at least 4-6 thread pitches. This amount of data is required to construct several of the intermediate data products with the required accuracy.

A third assumption is that the thread be manufactured with a 60-degree flank angle. Thread processing implicitly utilizes this parameter in several places. One of the most direct usages is the conversion of lead deviation into functional diameter.

A fourth assumption is that the thread has a cylindrical cross section. Non-cylindrical threads would require the 3-D peak cylinder to be suitably generalized. Incorrect fit to a non-cylindrical cross section would lead to incorrect lead deviation measures.

A fifth assumption is that the thread has a single helix.

Measurement of the following threaded fasteners are provided:
 non-standard thread types, especially self-tapping screws, small threaded regions with 2 or 3 pitches.
 Taptite trilobe threaded regions.

Rough Crossings

The thread model describes herein below is a sampled representation of one thread profile, for exactly one pitch. Thread model starts at the midpoint of a rising thread flank and ends one pitch later.

Using a correlation detector the thread model is matched to data within the inspection regions producing thresholded detections within the inspection region, that are called crossings.

"Refinements" noted herein may make the crossings more accurate. The refinements also separate the crossings into positive crossings and negative crossings. The thread model is a lateral sequence of points that represent a best estimate of the outline of one cycle of the thread form.

Rough Crest and Root Positions

A crest/root detector extracts rough crest and root positions between the matched adjacent pairs of positive and negative crossings.

Pitch Estimate

A pitch estimate is required for step set gage wire diameter. The estimate is required to be accurate enough to unambiguously select a unique gage wire from the set appropriate for the measurement. The current process utilizes a two-stage process.

This process may be simplified as described herein.

First estimate.

Crossing data is analyzed and averaged over all sensors to create a thread pitch estimate, the "crossing pitch."

Second Pitch Estimate

The steps set wire gage diameter, wire position search intervals, measure flank lines and measure 3-point diameters noted herein below are completed in a first iteration. Then the wire positions are averaged over all sensors and positions to compute a pitch estimate.

Set Gage Wire Diameter

Gage wires are utilized in physical thread measurements of pitch diameter in the prior art. Two wires are placed in adjacent threads on one side of the part, and a single wire is placed on the other side of the part. A micrometer measures the distance between the reference line established by the two adjacent gage wires and the reference point established by the other gage wire. A tabulated correction formula converts the micrometer distance to an estimate of the pitch diameter.

Gage wire sizes are thus selected prior to the thread measurement. To do this one estimates the thread pitch as previously described and then one selects the closest gage wire in a set to the pitch estimate. The gage wire set utilized is the one appropriate to the type of measurement; currently there is one set for the metric coarse thread sequence, and another for a similar English thread set. The gage wire sets are chosen at part template edit time by making a selection in a pull down list.

Wire position Search Intervals

One places "virtual" gage wires onto the calibrated sensor data throughout the inspection region. In order to place the "virtual" gage wires we must identify search intervals for each wire to be located.

A requirement of the following processing steps is that the wire positions in the inspection region have no gaps. Another requirement is that a wire position search interval consist of two valid thread crests, one valid thread root between the two thread crests, and valid positive/negative crossings between the crest/root pairs.

One then searches the set of positive/negative crossings and crest/root positions for the set of wire position search intervals to analyze. The result of intervals, one set per sensor.

Measure Flank Lines

For a left flank all data is analyzed between the rough positions of the left crest and the central root. One then determines the height limits of a flank line data extraction region that covers 70% (a configurable parameter) of the height interval between left crest and central root. This data is extracted into a data set and fit to a line, becoming the left flank line.

The procedure avoids the non-linear regions near the left crest and central root. In addition, a "flank line valid" flag is computed, based on the RMS distance between the left flank line and the data within the left flank line data extraction region. If the RMS distance between the flank line and the data points in the flank line data extraction interval is larger than 10 μm per point (a configurable parameter), then the flag is set to invalid.

The process is repeated for the right flank line and then for all wire position search intervals.

Measure Wire Positions

The wire positions are calculated, given the left and right flank lines and the wire size. The virtual wire is tangent to each flank line and the resulting position is calculated with a simple geometric formula.

The position has a valid flag that is true when both flank lines are valid, and false otherwise.

Measure 3-Point Diameters

The 3-point technique is a method to measure the minor, major, and pitch diameters without explicitly utilizing 3-D information.

For example, consider the major diameter. It is defined as the diameter of a cylinder that contains all the inspection region's thread crests.

In this method, the top of a thread crest in calibrated sensor coordinates forms an elementary measurement. The elementary measurements are combined into triplets for further analysis. Only crests from the two sensors of a single laser are combined.

Two adjacent thread crest positions are combined with the thread crest position that is closest to the average position of crests. The two crests form a reference line. Then the distance from the reference line to the crest is computed. This is the 3 crest distance for that crest triplet.

In this manner, the 3-crest distances from all adjacent crest triplets are computed. The 3-crest distances are all added to a data vector. The 3-crest diameter measurement is either the average or the median of all the 3-crest distances within the 3-crest data vector.

3-Point Minor Diameter

The 3-point minor diameter computes 3-point distances using precise root locations in the sensor data. The 3-point minor diameter is the average of the 3-point distance vector.

3-Point Major Diameter

The 3-point major diameter computes 3-crest distances using precise crest locations in the sensor data. The 3-point major diameter is the median of the 3-point distance vector.

3-Point Wire Pitch Diameter

The 3-point pitch diameter computes 3-point distances using the wire positions computed in the sensor data. The 3-point wire pitch diameter is the median of the 3-pointwire pitch diameter.

Figure 14:
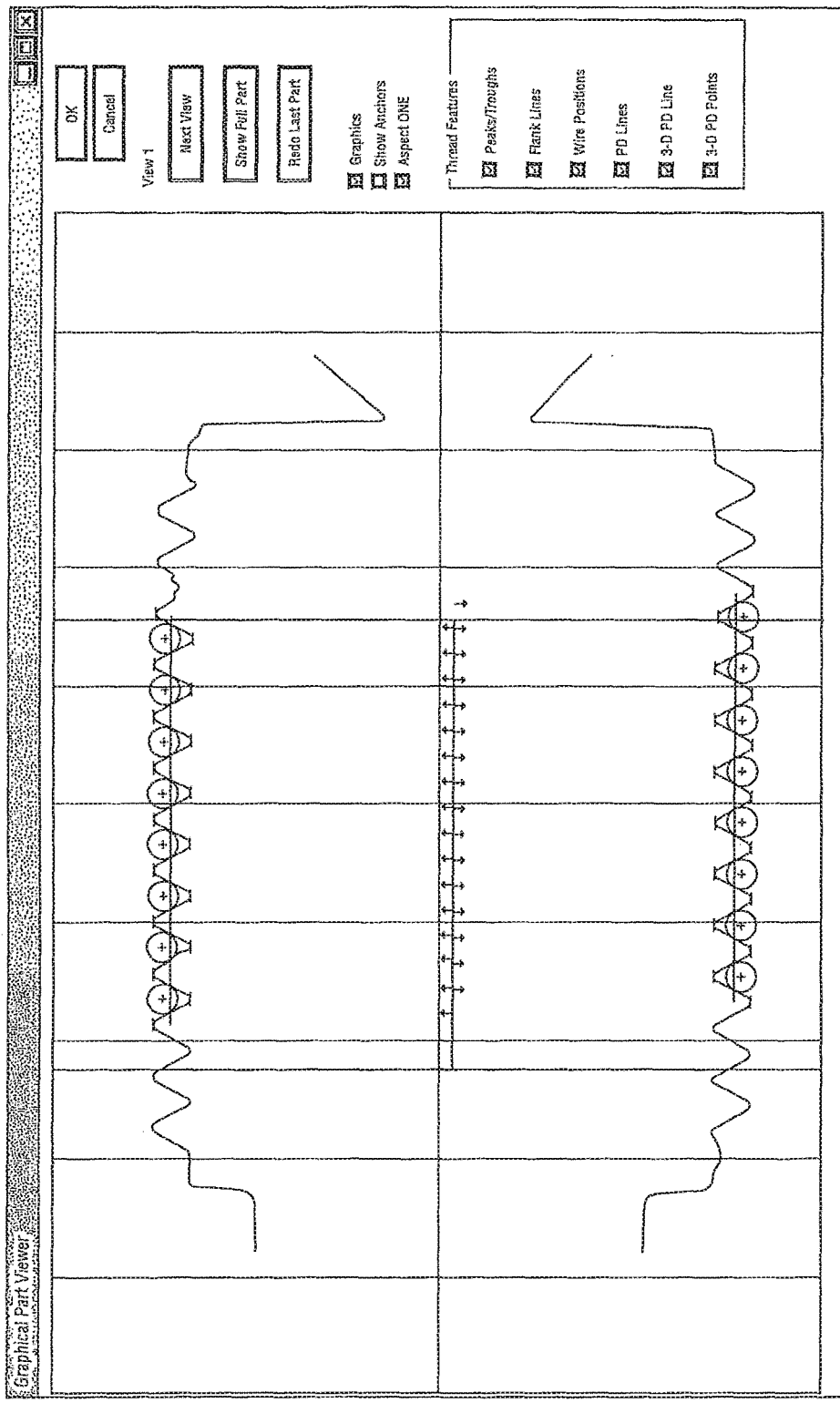
FIG. 14 is a screen shot of a graph of data with external wires with respect to a view of a threaded fastener.

FIG. 14 is screen shot from a user interface of a PC which illustrate intermediate data extracted from a M16×1.5 thread plug gage.

Measure 3-D Crest Cylinder

The measured thread crest position data is analyzed to obtain a 3-D cylinder with least squares methods. The 3-D crest cylinder fit has several output parameters of interest.

the RMS distance between the crest position data and the fitted shape.

the 3-D location of the cylinder's central axis.

the radius of the cylinder

Project Wire Positions onto 3-D Crest Cylinder Axis

Measured wire positions can be combined with the 3-D location of the 3-D crest cylinder's central axis. An imaginary disk, perpendicular to the cylinder axis that goes through the measured wire position marks a position on the 3-D crest cylinder axis.

A data set consisting of the projections of all sensor wire positions is constructed.

The output intermediate data is a vector, sorted from minimum to maximum sensor stage position of the projected wire positions.

Thread Parameter Estimation

Thread parameter estimation utilizes the intermediate data products and may also correct them based on a model of the measurement, prior to producing a final thread parameter estimate.

Wire Pitch

Thread pitch is estimated from the wire center intermediate data. For each sensor data set the adjacent pairs of wire positions are used to calculate an adjacent wire pitch, one per adjacent wire positions. For all lasers, each wire pitch is added to a wire pitch vector.

The wire pitch estimate is the median of the elements in the wire pitch vector.

Major Diameter

Thread major diameter is typically reported as the diameter of the 3-D crest cylinder.

If the 3-D crest cylinder fit was unsuccessful, the major diameter is estimated in a different way, detailed below. The cylinder fit can fail due to several factors listed here:

part inclined at too great an angle with respect to the stage axis.

thread crest positions do not fit a cylinder, the RMS fit-to-data distance is too large.

When the cylinder fit fails the major diameter is estimated from the 3-point major diameter data. This case is special because a previous condition (cylinder fit) has already failed. In practice, the cylinder fit most often failed when the threaded region was too short or the inspection extended beyond the end of the threaded region.

Because of this bias a simple median of the 3-point major diameter data would typically be too low, most of the good 3-point data was concentrated at the highest measurements. In this case the major diameter estimate is the value such that 20% of the 3-point data is higher and 80% of the 3-point data is lower.

Calibration Correction

Major diameter is also corrected by a final end-to-end calibration of the total system. The reported major diameter is often two low, with bias ranging from −20 μm to 0.

After diameter calibration the system is exposed to a set of measured thread plug gages. One then plots their major diameter bias as a function of diameter and fit a simple segmented line to the bias results. These bias fits then are entered into the system configuration file and are used to correct the measured major diameter with the measured bias.

Minor Diameter

Thread minor diameter is estimated with the 3-point minor diameter distance vector. The minor diameter value is the average of the elements in the distance vector.

Pitch Diameter

Pitch diameter estimation uses two sets of intermediate data products, the wire positions and the 3-D crest cylinder fit.

The pitch diameter estimate calculation is presented in a step-by-step list below:

a) Compute the pitch diameter contact points with the thread flanks by calculating the intersection of the wire shape with the left or right flank lines.

b) Average the left and right points of intersection, and compute the distance (radius) from the average point to the 3-D crest cylinder fit axis. This is the pitch diameter radius for each wire position.

c) Calculate the average value of the pitch diameter radius.

d) Correct each average wire position radius for the part projection angle, using the angle of the 3-D crest cylinder axis to the stage axis, projected into the sensor's coordinate system.

e) Add left and right sensor corrected pitch diameter radius estimates to product an estimate of the pitch diameter for each view.

f) Average the laser estimates to produce the system pitch diameter estimate.

Correction for Part Projection Angle

The computation of pitch diameter is complicated by projection effects. The light performs an almost perfect orthographic (shadow) projection of the thread's shape. However, the projection is not the same thing as the thread cross section, which is specified in thread design documents. The cross section is the thread shape if it were cut by a plane going through the thread's central axis.

The difference is caused by the thread lead angle, which is in the range of 1-3 degrees for many typical threads. The lead angle means that the thread cross section is most accurately viewed in shadow when the viewing direction coincides with the direction of the lead.

It is impossible to position the thread so that a shadow view of the thread is simultaneously aligned with the top and bottom threads. For the example of a thread with a 3 degree lead angle, tilting the thread to align the top of the thread with the viewing angle will make the angle between the lead and the viewing angle for the bottom thread about 6 degrees.

A correction factor was developed for this effect. If one knows to tilt of the thread with respect to the viewing angle then you can correct the observed pitch diameter radius for the expected bias caused by the projection angle. This correction is precomputed and stored in a table.

For each view the tilt of the thread with respect to the viewing angle can be obtained from the 3-D cylinder fit axis. Separate corrections are applied for the different views.

Calibration Correction

Pitch diameter is also corrected by a final end-to-end calibration of the total system. The reported pitch diameter is often too high, with bias ranging from +5 μm to +35 μm.

After diameter calibration, one exposes the system to a set of measured thread plugs gages. One then plots their pitch diameter bias as a function of diameter and fit a simple segmented line to the bias results. These bias fits then are entered into the system calibration file and are used to correct the measured pitch diameter with the measured bias.

Lead Deviation

The lead deviation estimate uses the wire pitch and the locations of the wire positions as projected onto the 3-D cylinder fit axis.

For an ideal helical thread, the wire position projections should result in a regular pattern along the 3-D cylinder fit axis. Lead deviation is the deviation of that pattern from the ideal, measured as a maximum distance of any projected wire position from the ideal pattern.

The computation of the lead deviation estimate follows a step-by-step procedure:

a) Create a wire position projection vector, containing all the data.

b) Sort the wire position projection vector in order of position along the 3-D cylinder fit axis.

c) Convert the wire positions of the elements of the vector into degrees, by multiplying by the factor (360/pitch) and then reducing the element values modulo 360.

d) Calculate an offset value so that the maximum absolute value of the degree-valued element positions is minimal. For example with a lead deviation of 0.010 mm for a 1 mm pitch thread, the absolute value of at least one degree value element position would be 3.60 degrees (0.010) mm/1 mm equals (1/100) and 360/100 is 3.60)

Convert the value from degrees to mm and report as the lead deviation estimate.

All lead deviation estimates are positive.

Calibration Correction

Errors in measurement mean that the physical measurement of a perfect thread will have a positive lead deviation.

To attempt to correct for this effect, one measures the lead deviation for a set of thread plug gages and plotted them as a function of gage diameter. The most common form observed is a constant lead deviation of 0.010 mm to 0.20 mm.

This value observed in calibration with thread gages is taken to be a bias. This amount of bias is entered into the system calibration file and used to correct the measured lead deviation for this measurement bias.

Functional Diameter

Functional diameter is currently defined in practice by the fit of a special fit gage over the thread. The special fit gage is essentially a nut that is split in two by a plane cut through the central axis of the nut. The two halves of the fit gage are held in a fixture that measures the distance between the two halves. There is one special fit gage for every thread type.

Functional diameter is defined as the pitch diameter when the special fit gage is clamped tightly over a thread plug setting gage. When one puts a different part into the fit gage the fit gage may expand slightly, due to a summation of effects involving the differences between the part and the thread plug setting gage used to setup the functional diameter measurement. The functional diameter measurement is then the thread plug setting gage's pitch diameter plus the additional separation between the two fit gage pieces.

Functional Diameter Estimator

The functional diameter measurement method is an approximation of the fit gage method. We do not perform a full 3-D analog of the physical fit gage. Instead we have made an approximation that involves the use of lead deviation and the shape of the thread form.

If we imagine the thread form as perfect and also having a 60 degree flank angle then lead deviations should cause the thread form fit gage pieces to move apart. A single lead deviation either up or down the thread form axis will cause a single split piece of the fitting gage to move outward. The amount of outward movement for a 60 degree flank angle will be equal to ($\sqrt{3}$) (lead deviation). The movement provides a clearance for both positive and negative movements of the lead, relative to a perfect helical shape.

$$FD=PD+\sqrt{3}(\text{LeadDeviation})$$

Learning the Thread Model

The thread model is a learned sequence of points that represent a best estimate of the outline of one cycle of the thread form. The thread model is calculated when the inspection region is specified, at template edit time.

The measure template routine uses a pattern match algorithm with a sine wave pattern to identify periodically in the inspection region data. This process determines an approximate thread pitch. The process also calculates a starting point in the data vector for the first beginning of the matched pattern, which is an approximation to the first midpoint of a right flank line.

With the pitch and the starting point in hand, the measure template routine can then calculate an average thread model. Starting with the first sample point in the matched pattern, points that are 1, 2, 3, . . . , N pitches later in the inspection region are averaged to form the first point of the thread model. The process is repeated for all the rest of the points in the first matched pattern. The thread model is then stored in the template for later use.

An alternative embodiment of the invention is illustrated in FIGS. 15-21. This embodiment is an inspection system and method that uses gravity to feed headed manufactured parts (e.g., hex headed bolts, ammunition cartridges, and the like) along an inclined track through an inspection station for optical inspection for conformity to dimensional and visual standards.

Figure 15:
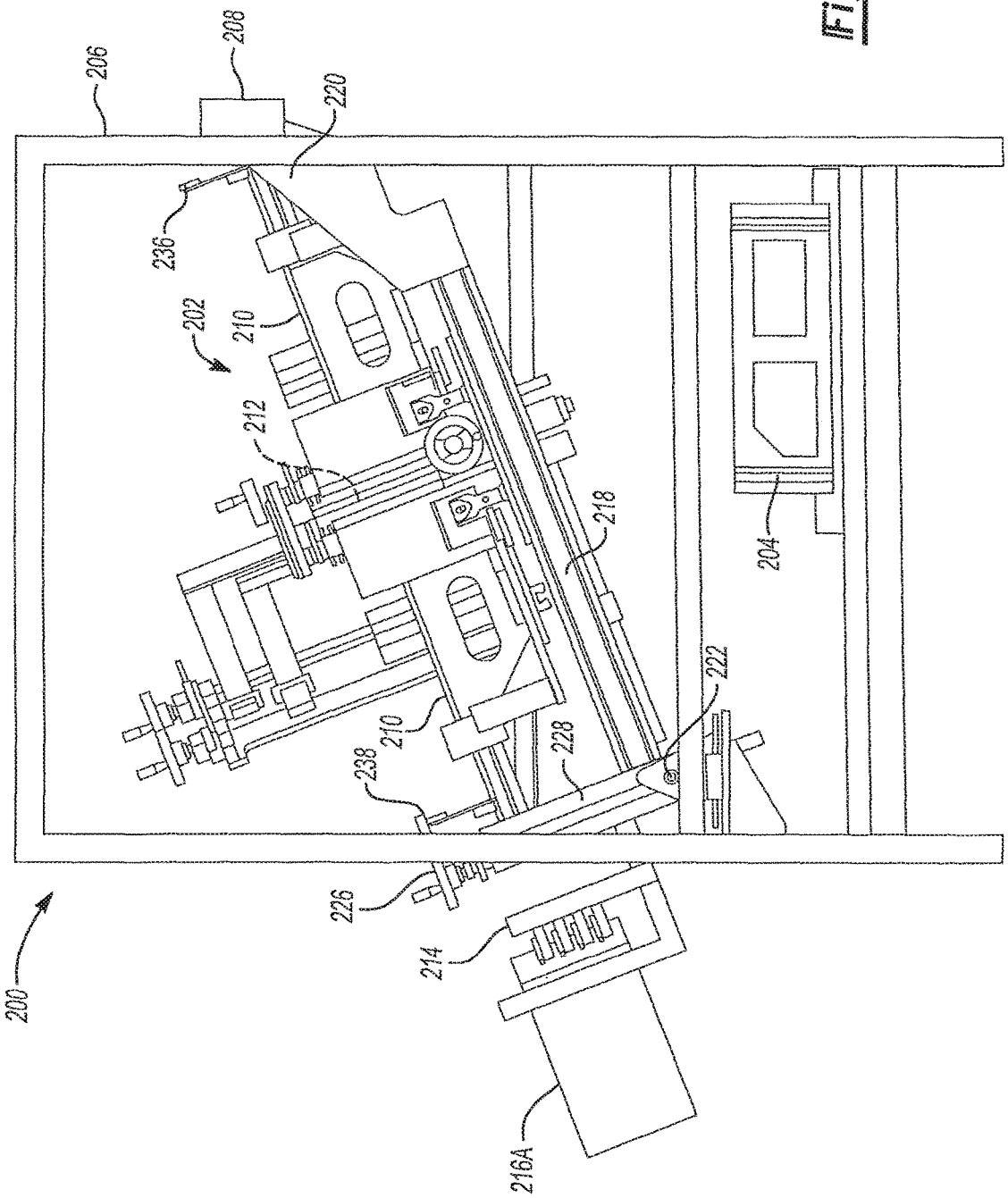
FIG. 15 is a side elevational view of another embodiment of a system of the present invention particularly suited for inspection of headed manufactured parts.

In FIG. 15, the optical inspection system is indicated generally at 200. A split track-based inspection apparatus is indicated generally at 202. A processor 204 executes the inspection process. The inspection apparatus 202 and processor 204 are mounted within a frame 206.

Figure 17:
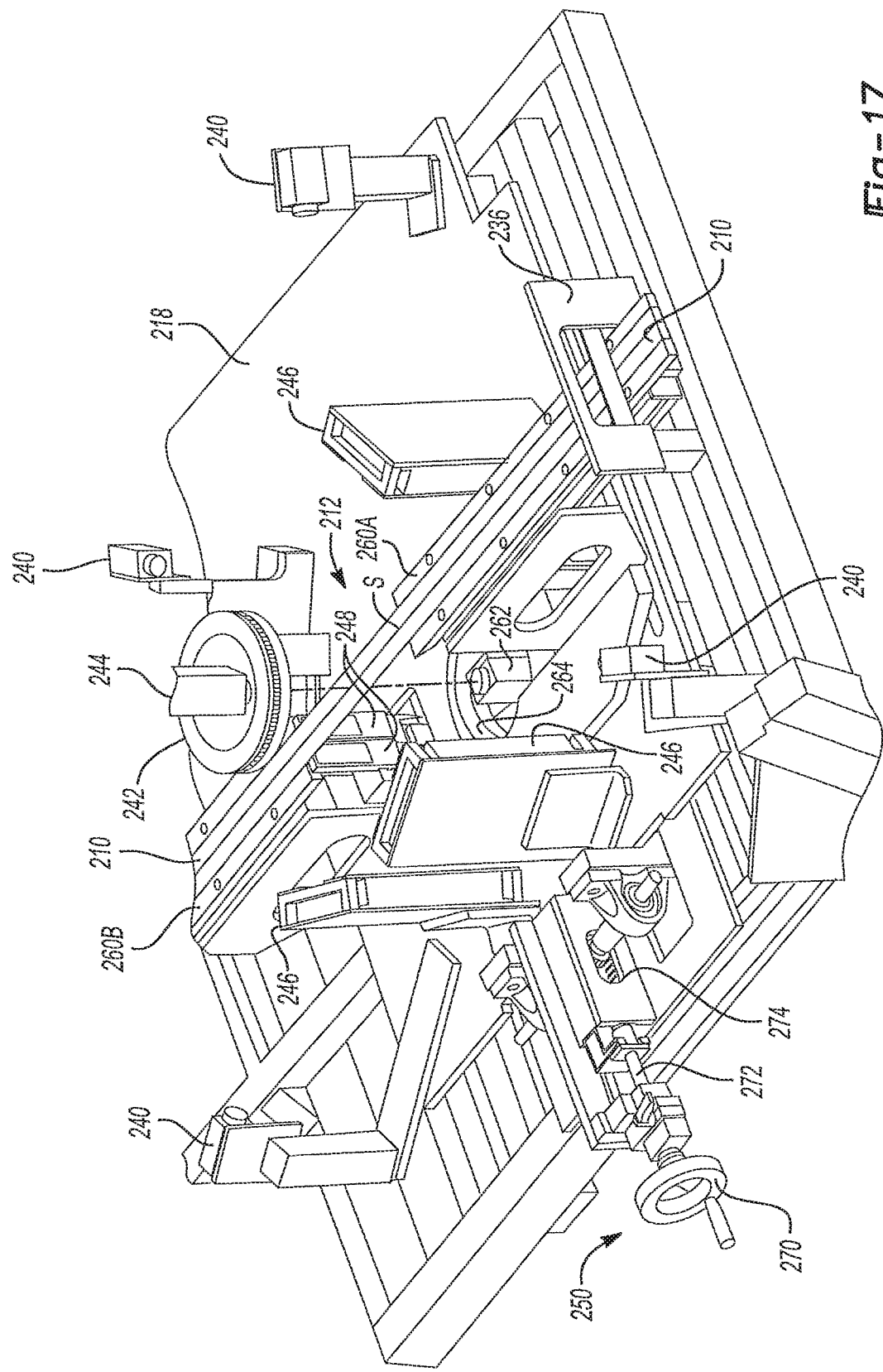
FIG. 17 is a plan perspective view, partially broken away, of the inspection system of FIG. 15, with the track for the headed parts in closed position.
Figure 18:
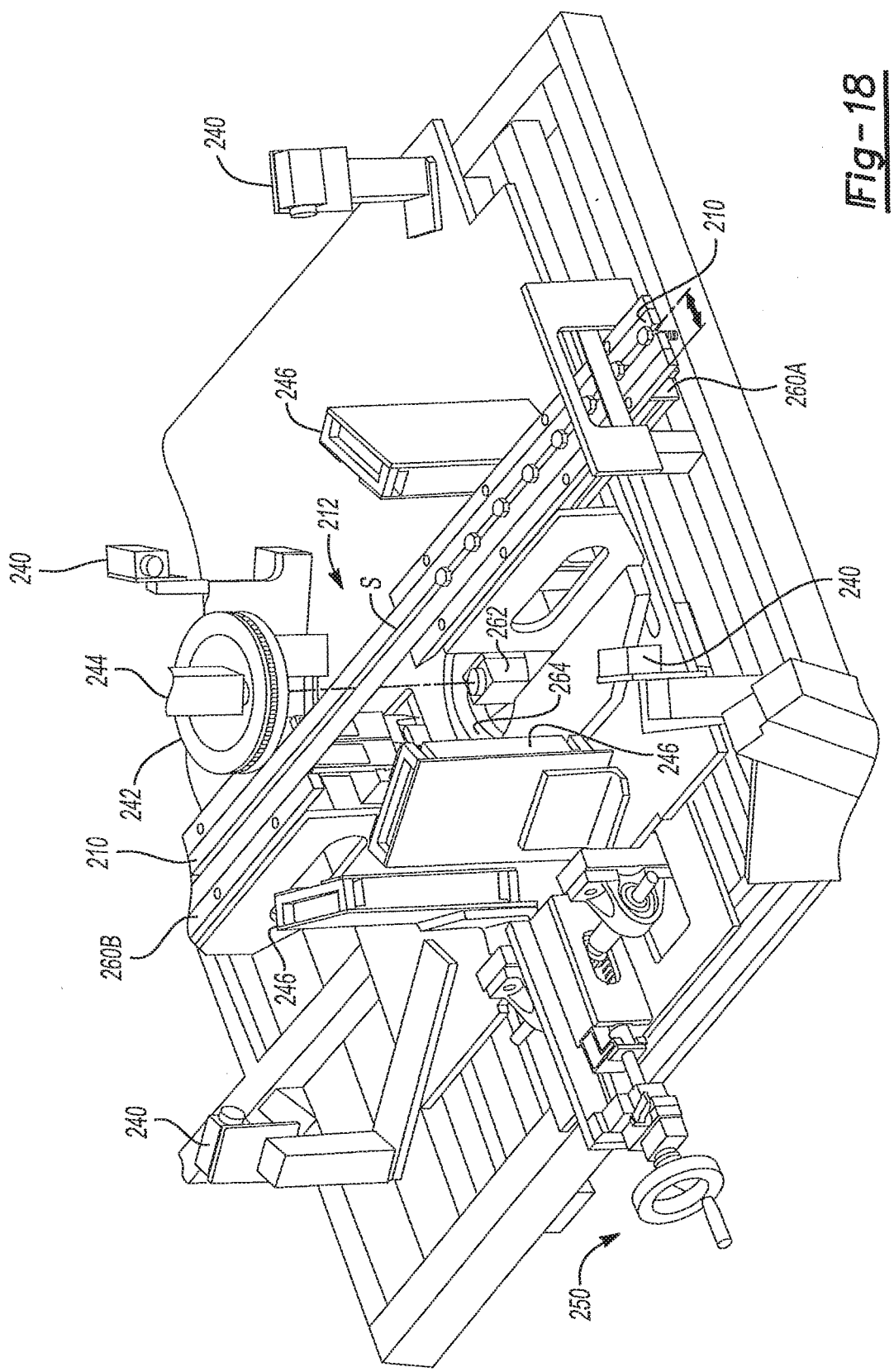
FIG. 18 is a plan perspective view, partially broken away, of the inspection system of FIG. 15, with the track for the headed parts in an open position.

Headed manufactured parts, e.g., hex headed bolts, are fed by a conventional hang-by-head feeder (see, U.S. Pat. No. 6,787,724) at a metered rate into a feed entrance 208. A hang-by-head split track 210 receives the parts and carries them by their heads. See bolts 234 in FIG. 18. The split track 210 is in three segments, as more particularly shown in FIGS. 17 and 18. A first segment upstream of an inspection station 212 is supported by undergirding 260A. A second segment, denoted by S in FIGS. 17 and 18, is a span of only the parallel rails of the split track through the inspection station 212. A third segment downstream of the inspection station 212 is supported by undergirding 260 B. This construction tends to minimize sagging of the split track 210 while maximizing exposure of the surfaces of the part while in the inspection station 212.

At the terminus of the split track 210 is an air blow off device 214, which effectively functions as a type of reject mechanism. In a preferred embodiment, the air blow off device 214 is actuated by the processor 204 to divert a headed part into a "good parts bin" (shown as 216B in FIGS. 16 and 21) if the part is determined by the processor to conform to dimensional and visual standards. However, if the part fails to conform to the standards, it is routed directly into a "bad parts bin" (shown as 216A in FIGS. 15, 16 and 21).

The preferred embodiment for the parallel rails of the split track 210 are stainless steel liners. The coefficient of friction should be consistent along the length of the split track 210. The stainless steel liners can be replaced after routine wear.

Optional embodiments for the parallel rails of the split track 201 are filamentary materials, such as piano wire, or monofilament fishing line. Another option is clear polycarbonate. These materials offer the potential for enhanced exposure of the bearing surface of the headed part while in the inspection station 212.

The inspection apparatus 202 is supported on an inclined table 218. The table 218 has a hinged connection to the frame 206, best seen in FIG. 16. Supporting arms 220 are fastened at to the upstream end of the table 218. The arms 220 have a hinged connection 232 to the frame 206 at the other end. In this manner, the feed height at the entrance 208 is maintained.

At the other end of the table is a slotted mounting track 228 to allow for adjustment of the angle of the table 218 (and, the angle of the split track 210, as well). The slotted mounting track 228 has a mounting fixture 222 at its lower end. The mounting fixture 222 includes a pin that fits within the slot in the mounting track 228. A hand wheel 226 is rotatable to move the mounting track 228 up or down to adjust the angular position of the table 218.

The inclined table 218 is adjustable through a nominal angular range of 15° to 35°. The angle of the table 218 can be set based on preliminary trial-and-error testing of the optimal angle for the specific type of headed parts to be inspected by the system 200.

Optical sensors 236 and 238 are at each end of the split track 210. The entry sensor 236 is responsive to a headed part entering the track, and sends a signal to the processor 204 informing of the introduction of the part into the inspection apparatus 202 in the queue of parts. The end sensor 238 is responsive to a headed part having passed the inspection station 212 and reached the end of the track 210. The end sensor 238 sends a signal to the processor informing of the exiting of the part from the split track 210. The processor 204 then sends a signal to the air blow off device 214 telling the device whether to divert the part, if a good part, or allow it to pass, if a bad part. This signal follows a determination made by the processor 204 based on the imaging of the headed part when passing through the inspection station 212.

Figure 16:
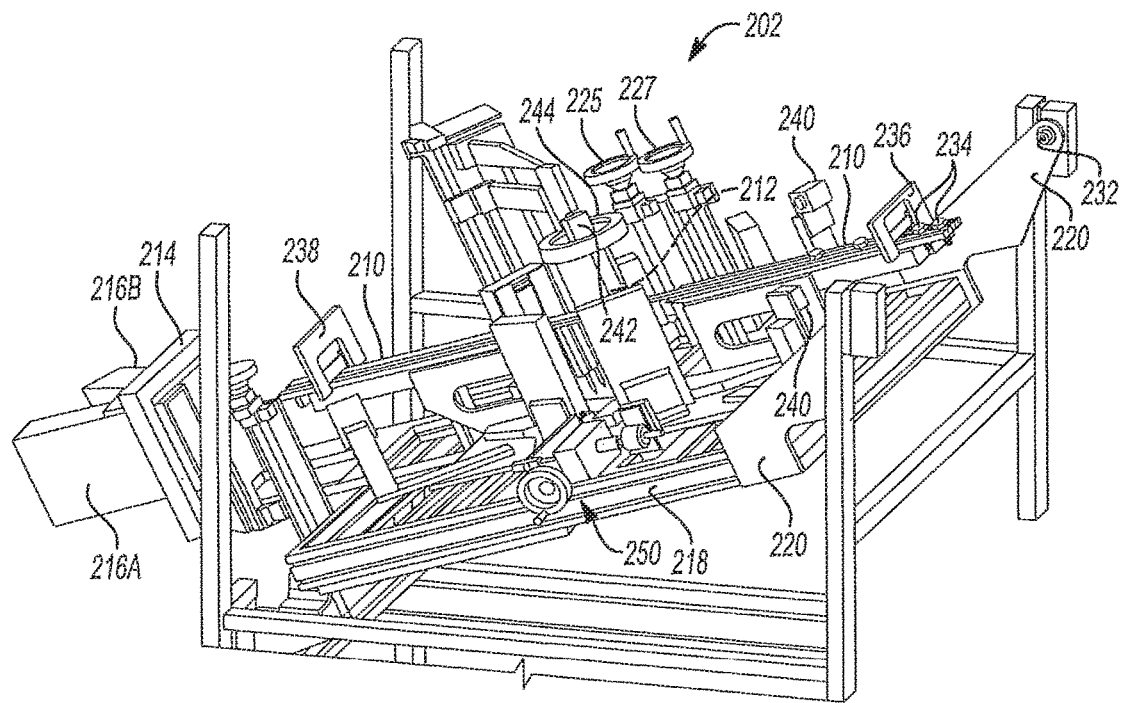
FIG. 16 is a side perspective view, partially broken away, of the inspection system of FIG. 15.
Figure 19:
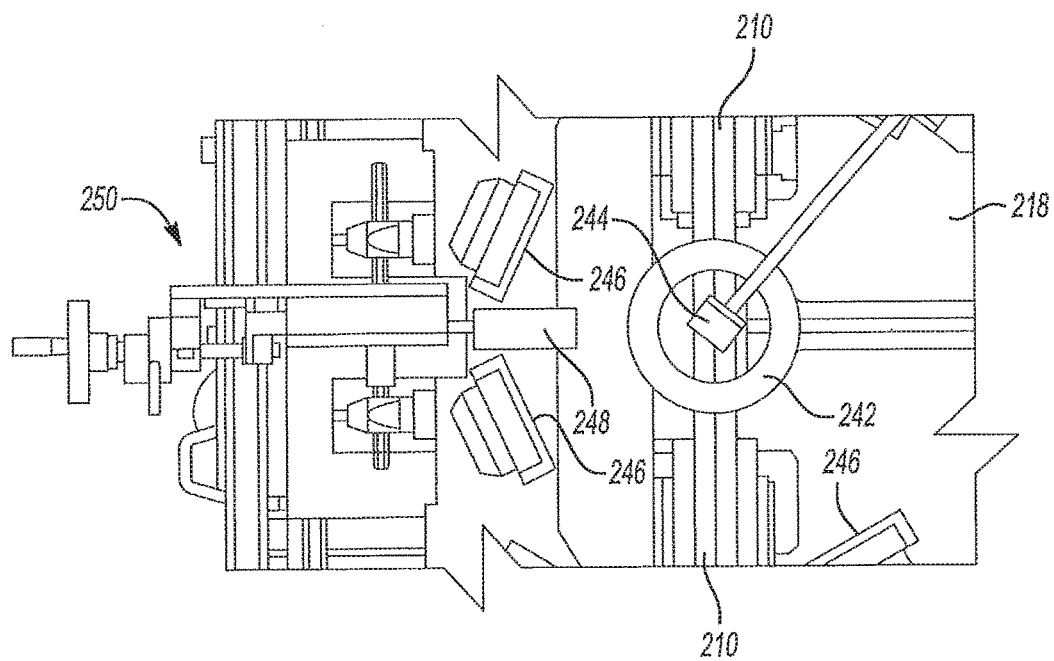
FIG. 19 is a plan view, partially broken away, of the inspection system of FIG. 15, with the track for the headed parts in closed position.

FIGS. 16-18 are perspective views, and FIG. 19 is a plan view, of the inspection apparatus 202, showing additional components.

In FIG. 16, an array of four cameras 240 are shown spaced 90° from one another. Each camera 240 is preferably a USB3 camera wired to the processor 204. The 90° spacing allows each camera 240 to image a quadrant of the headed fastener when in the inspection station 212.

An upper ring light 242 is centered about the vertical axis of the inspection station 212.

An overhead camera 244 is mounted centrally of the ring light 242. A pair of hand wheels 225 and 227 allow for adjustment of the vertical positions of the bottom camera 262 and the ring light 264, respectively. The overhead camera 244 has a pericentric lens that images the top and side surfaces of the headed part. A pericentric lens module is available from LIGHT WORKS, LLC, Toledo, Ohio 43615, under the model designator "Hyper-Eye." www.1w4u.com.

FIG. 18 shows a lower camera 262 centered within a lower ring light 264. The lower ring light 264 and the upper ring light 242 are strobed while the headed part is in the image plane of the cameras within the inspection station. A second pair of hand wheels (not shown) allow for adjustment of the vertical positions of the upper ring light and the upper camera, respectively.

In FIG. 17 is shown a mechanism 250 for adjusting the width between the rails of the split track 210 to fit the diameter of the shank, casing or cylindrical body of the manufactured headed parts to be inspected. One side of the track 210 is movable on a slide below the table, and the other side is fixed. The slide is connected to a lead screw (not shown) that is advanced or retracted by a hand wheel 270 that turns a shaft 272 connected to the lead screw through a rack-and-pinion gear set 274.

The upper ring light 264, upper camera 262, lower ring light 242 and lower camera 244, are also mounted on movable slides. The ring lights 242 and 264 and cameras 244 and 262 must be moved by one-half of the displacement of the movable side of the track 210 to keep them centered in the inspection station. This is accomplished through reduction gearing on parallel shafts. See Harold A. Rothbart, MECHANICAL DESIGN AND SYSTEMS HANDBOOK, 2d. Ed., Ch. 38.3.1 "Parallel Shaft Gear Types," McGraw-Hill 1985.

FIGS. 17-20 show an array of strobe lights 246 are mounted on the table 218. The strobe lights 246 illuminate the sides of the headed part.

Figure 20:
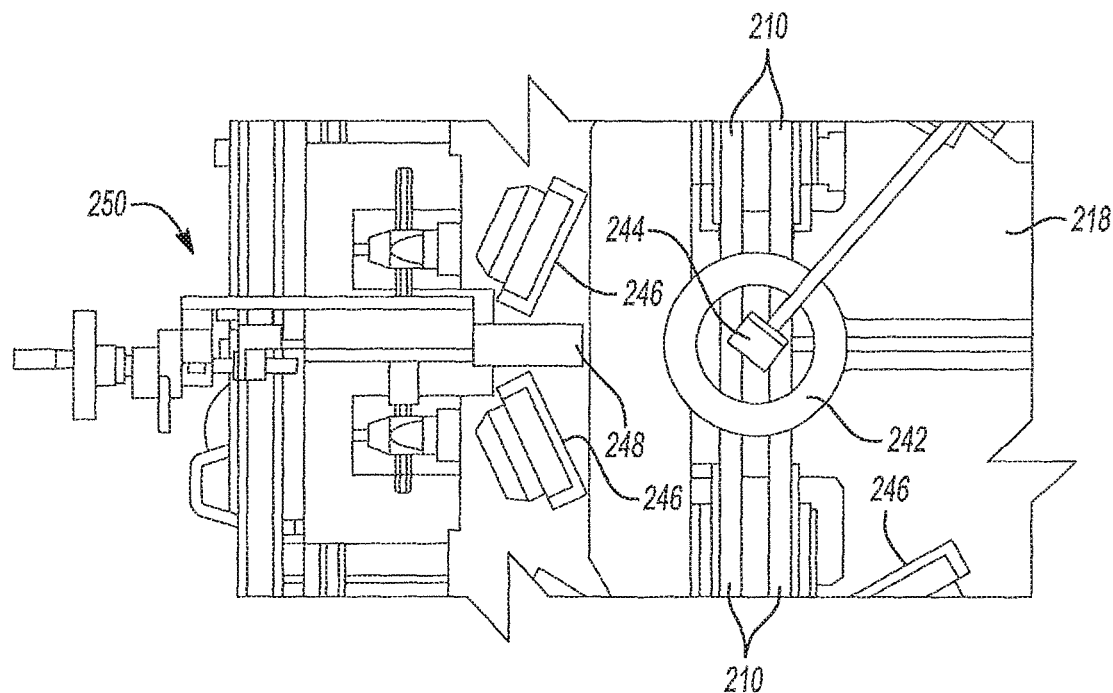
FIG. 20 is a plan view, partially broken away, of the inspection system of FIG. 15, with the track for the headed parts in an open position.

FIGS. 17, 19 and 20 show an eddy current detection coil 248 positioned within the inspection station 12 to detect eddy current defects.

Figure 22A:
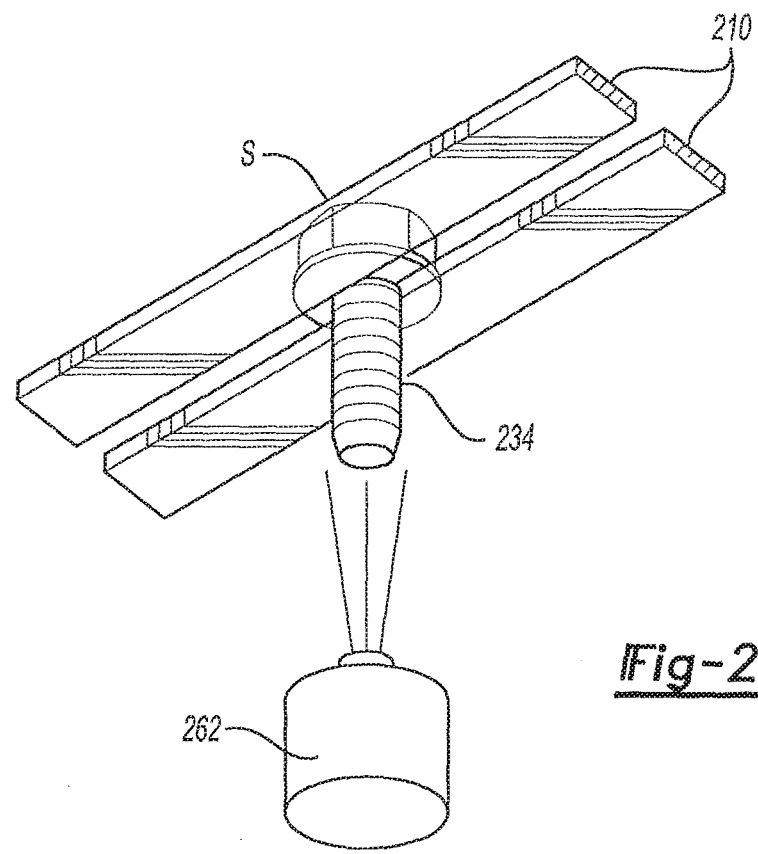
FIG. 22a is a schematic view of a segment of the track formed of a transparent material to permit imaging of the underside of a hex headed bolt.
Figure 21:
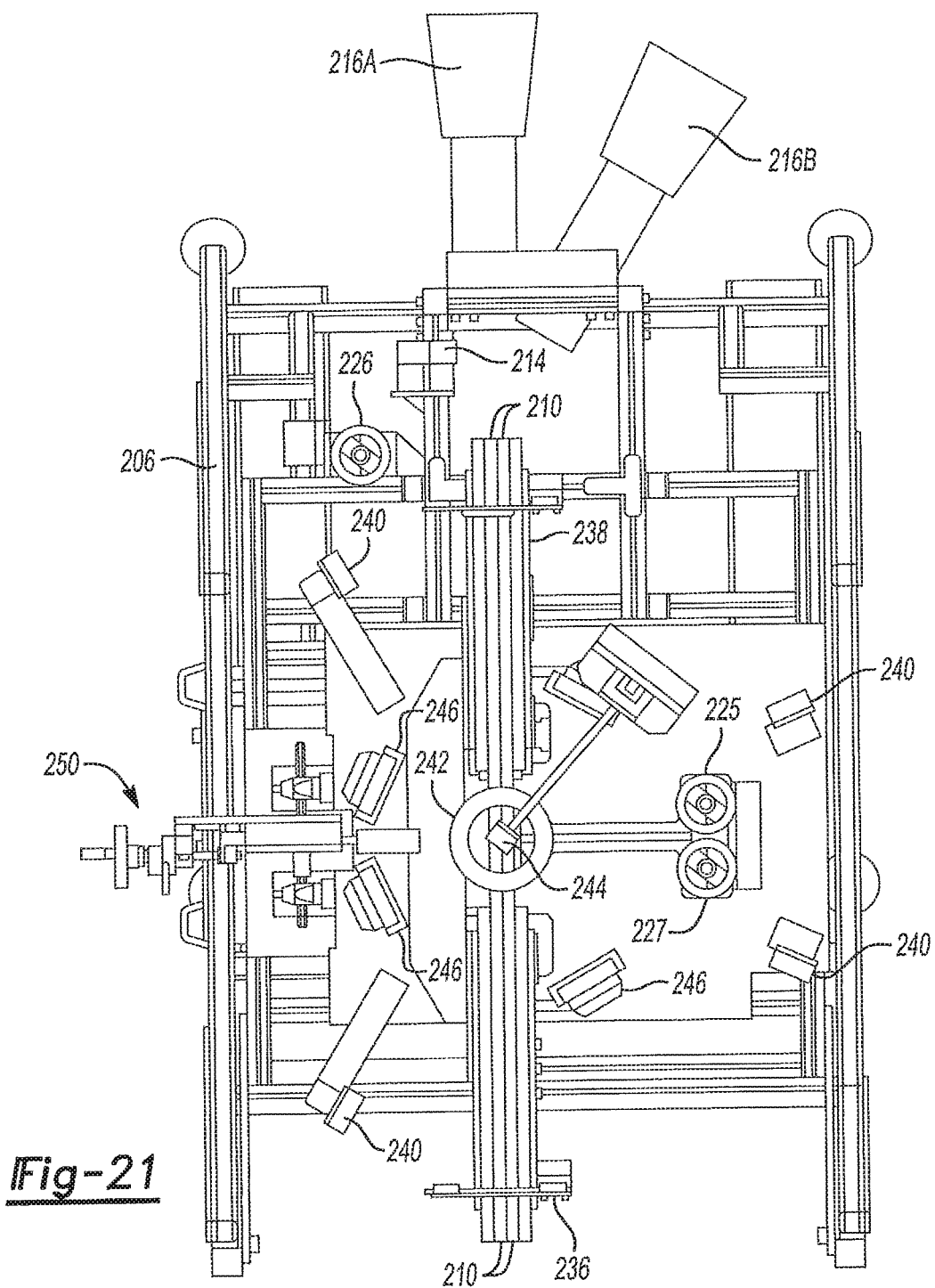
FIG. 21 is a diagrammatic plan view of the inspection system of FIG. 15.

FIG. 22A shows in schematic form a segment S of the split track 210 having transparent rails. The transparent rails permit the underside bearing surface of the bolt 234 to have enhanced exposure to the lower camera 262.

Figure 22B:
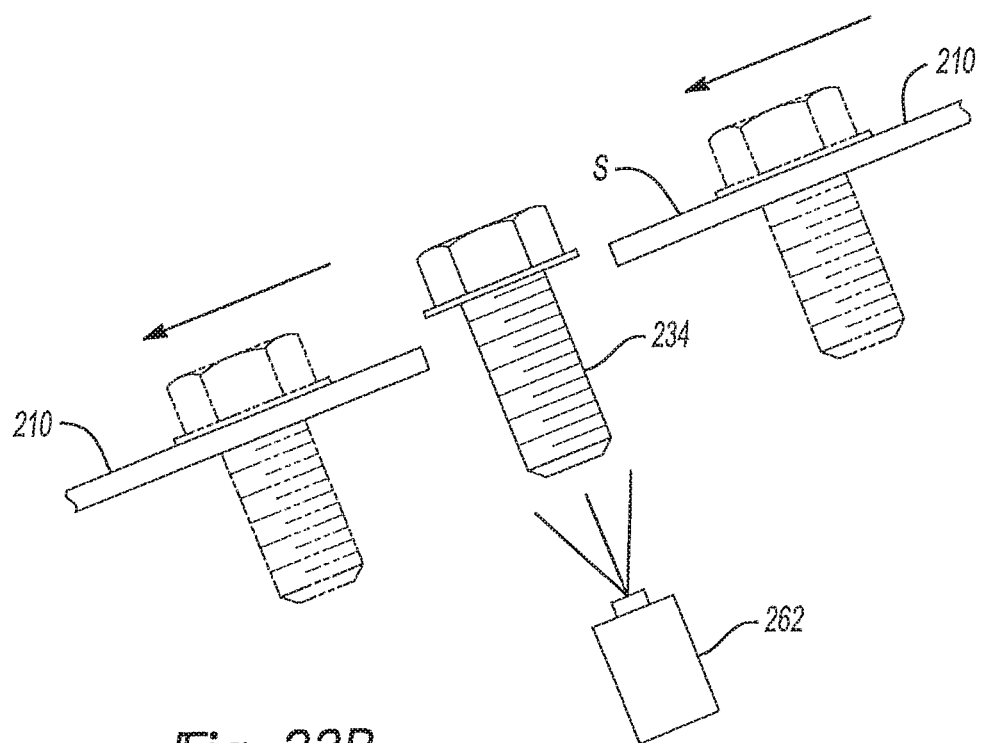
FIG. 22b is a schematic view of a segment of the track having a separation gap wider than the width of the bolt head to permit the bolt to traverse the separation gap and permit imaging of the entire underside of a hex headed bolt.

FIG. 22B shows in schematic form a segment of the split track having a gap in the track 210 of sufficient width to permit the bolt 234 to traverse the gap unsupported. This feature permits the entire underside of the bolt head, i.e., bearing surface, to be in the field of view of the camera 262. The downstream side of the track 201 is lowered slightly to accommodate the free fall of the bolt 234 while traversing the gap.

Figure 22C:
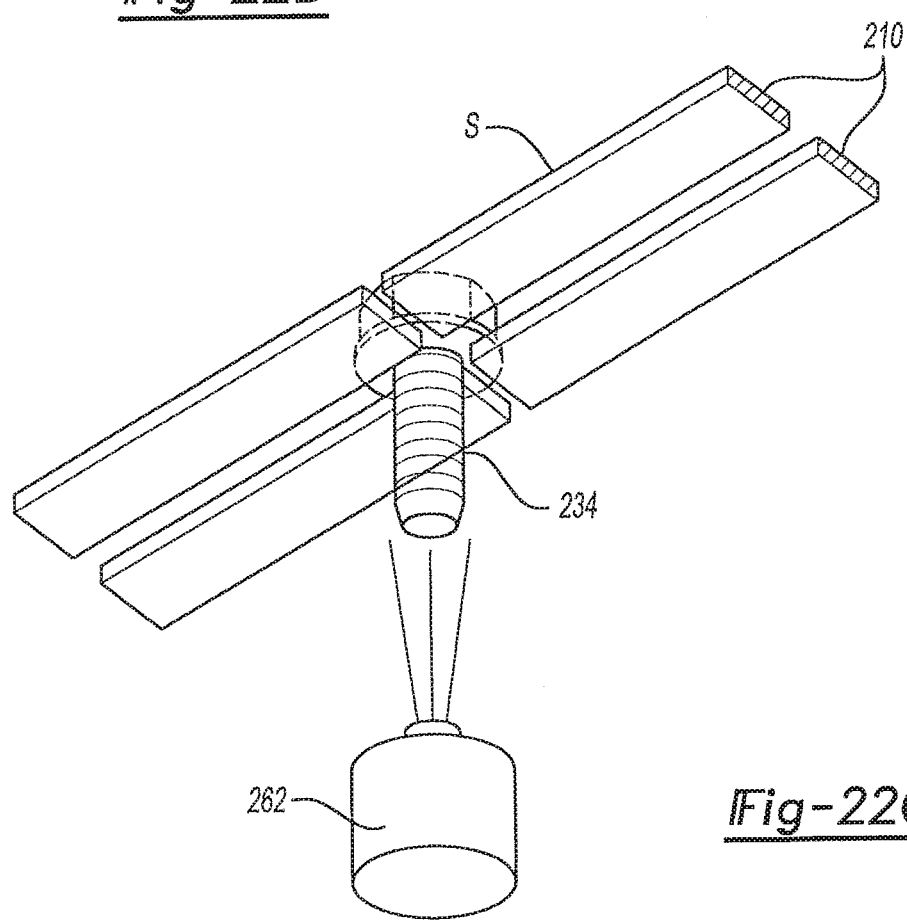
FIG. 22c is a schematic view of a segment of the track having a separation gap narrower than the width of the bolt head to permit line scan imaging of the underside of a hex headed bolt.

FIG. 22C shows in schematic form a segment of the split track 210 having a relatively shorter gap that permits the bearing surface of the bolt to be successively imaged by line scans as it traverses the shorter gap. In this embodiment the camera 262 is a line scan camera.

If desired a friction-reducing coating can be applied to the rails, e.g, a boron-based formulation as disclosed in U.S. Pat. No. 7,811,975, titled "Metalworking and Machining Fluids."

Figure 23:
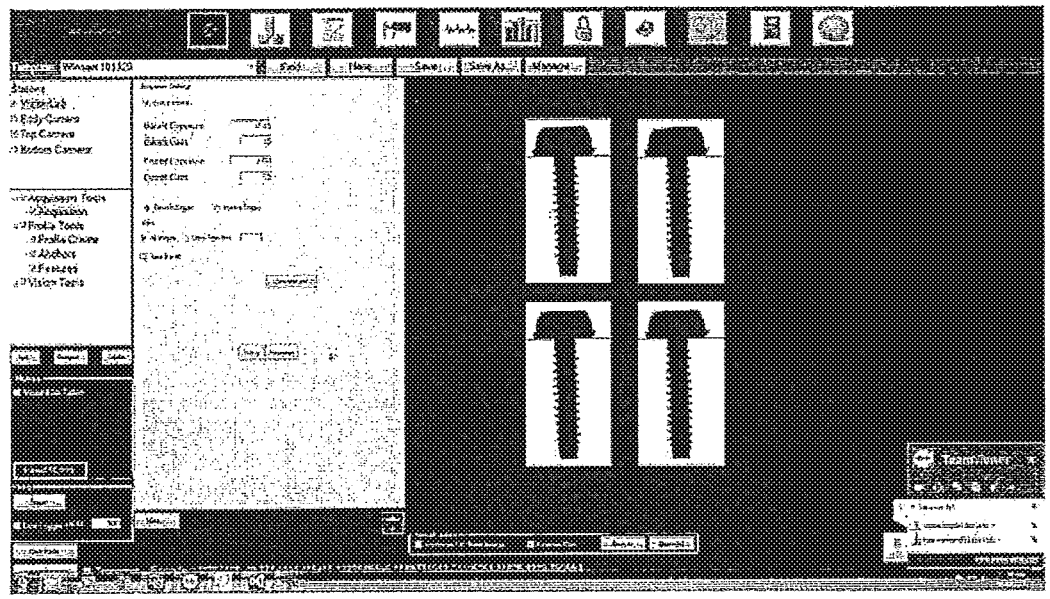
FIG. 23 is a screen shot of the images of four quadrants of a headed fastener obtained by backlighting the fastener and capturing the quadrant images.

FIG. 23 is an exemplary screen shot of the four quadrants of a headed fastener imaged in the inspection station by the cameras 240. The images are obtained by firing strobe lights 246 while the fastener is in view of the cameras 240, and capturing the light not occluded by the fastener. The quadrant profiles of the fastener can be compared to standard dimensional attributes of the fastener by the processor 204 to determine if the fastener dimensions conform.

Figure 24:
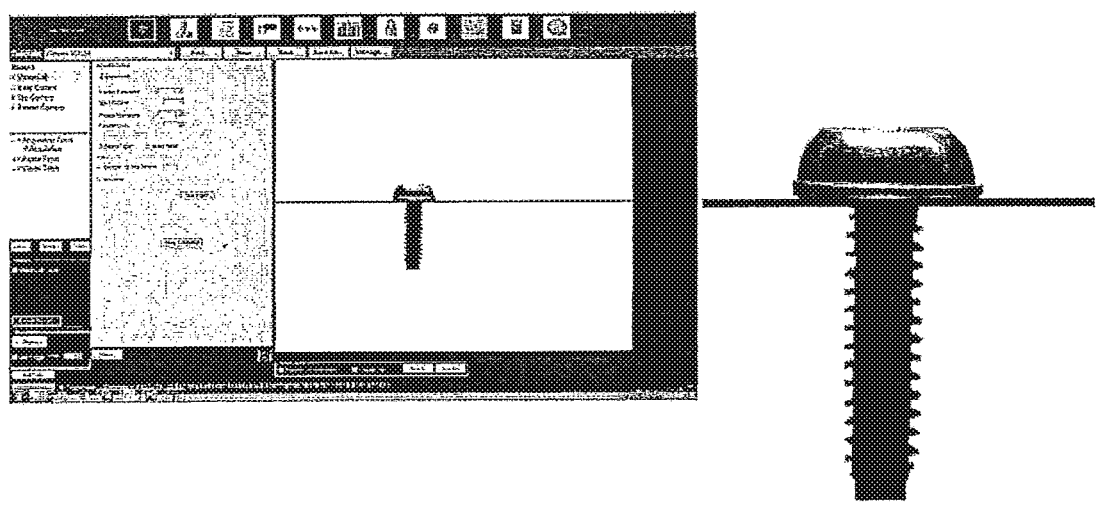
FIG. 24 is a screen shot of an image of a fastener obtained by direct reflection of light from the fastener.

FIG. 24 is an exemplary screen shot of one quadrant of the fastener consecutively imaged in the inspection station by the cameras 240. The images are obtained by firing the upper and lower ring lights 242 and 264 while the fastener is in view of the cameras 240, and capturing light reflected by the fastener. The quadrant profiles of the fastener using reflected light images can be compared to standard visual attributes of the fastener by the processor 204 to determine if the fastener conforms, i.e., does not have cracks, scratches, flange or washer defects, or missing features.

Figure 25:
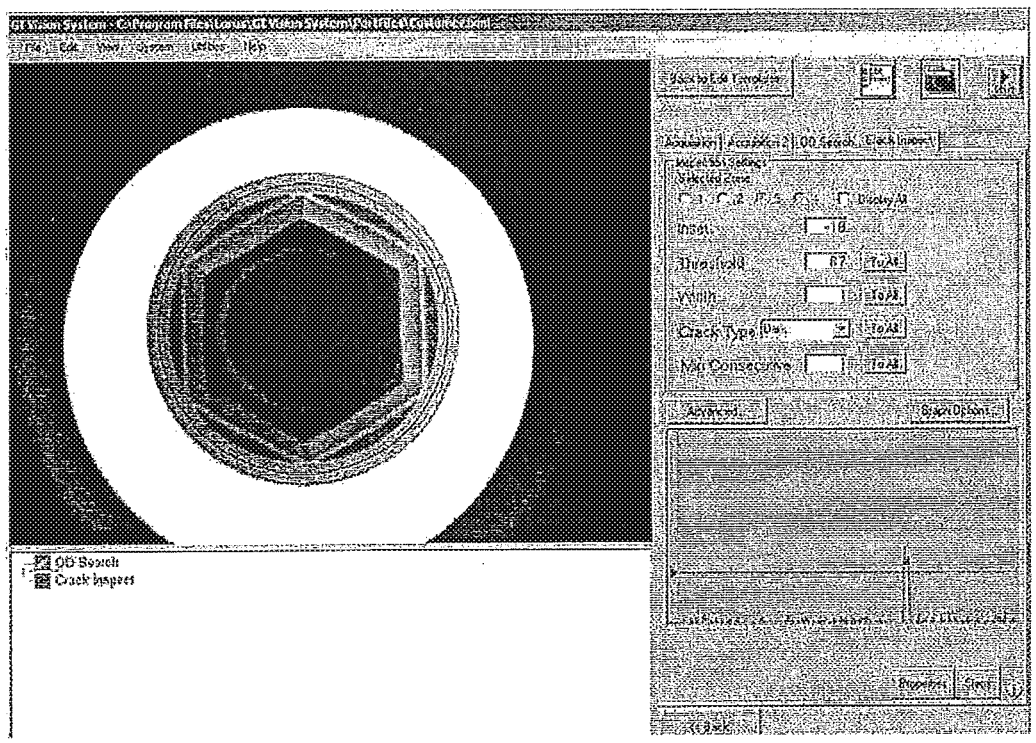
FIG. 25 is a screen shot of the top and side surfaces of the head of a hex headed bolt obtained by a top axial view through a pericentric lens.

FIG. 25 is a screen shot of the image of the top and side surfaces of the headed fastener obtained through the camera 244 equipped with a pericentric lens. This image is also communicated to the processor 204 for comparison to standard visual attributes of the top and side surfaces of the fastener head to determine if the fastener conforms.

Figure 26:
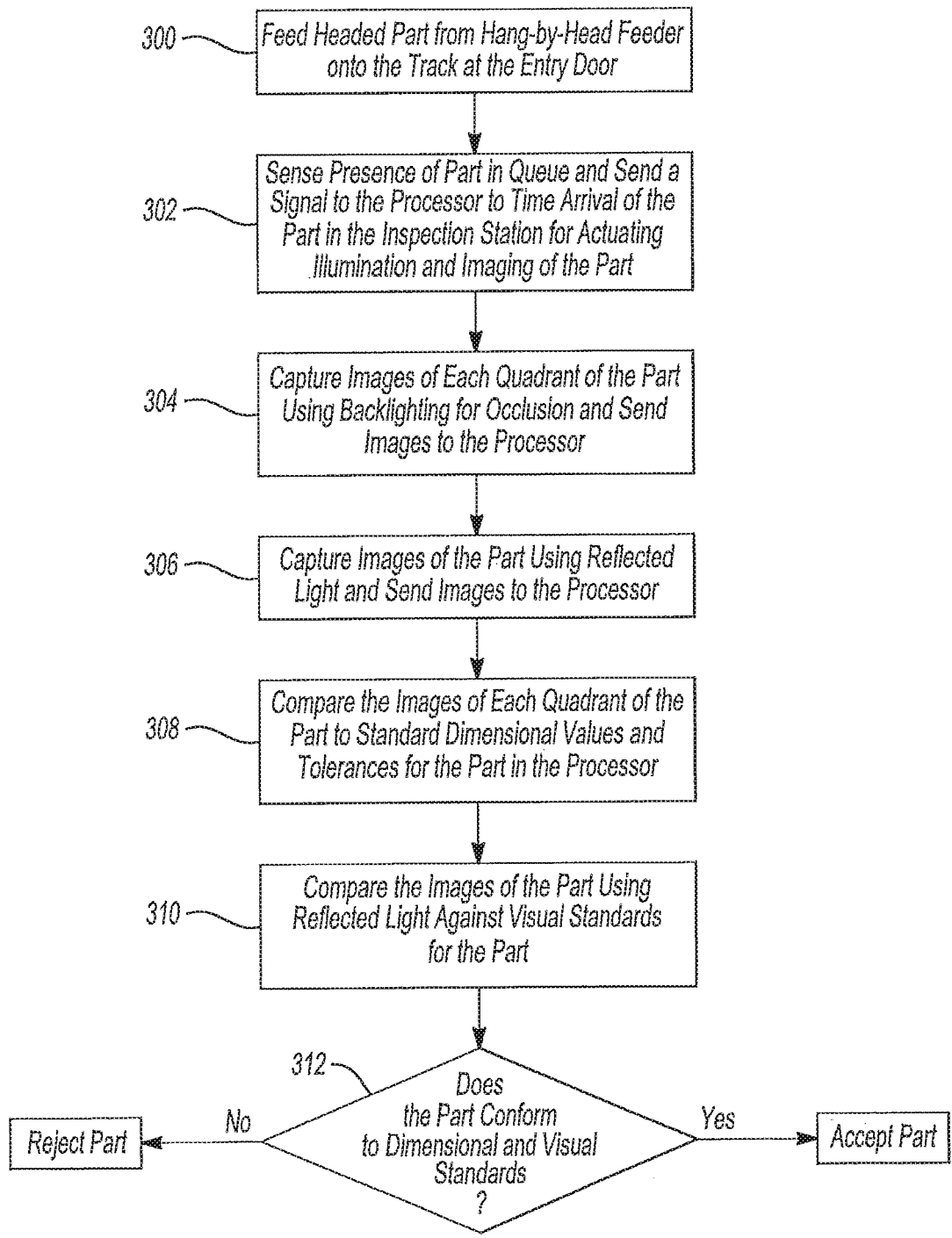
FIG. 26 is a flowchart of the operational steps and program logic used in inspecting and sorting headed parts in the inspection system of FIG. 15.

FIG. 26 is a flowchart showing the operational steps of the inspection machine 200, and the processing implemented in the programmable logic of the controller 204.

In step 300 a headed part is fed into the entry door by a conventional hang-by-head feeder.

In step 302 the presence of the headed part in the queue is sensed and a signal is sent to the processor to time the arrival of the part in the inspection station.

In step 304 the mounted strobe lights surrounding the inspection station are fired while the part is in view of the cameras within the inspection station. The four cameras spaced 90° each capture the image of a quadrant of the part using occluded light, and send the images to the processor.

In step 306 the strobe ring lights above and below the inspection station are fired while the part is in view of the cameras within the inspection station. Both the upper and lower cameras and the four cameras spaced 90° capture images of reflected light from the aspects of the part, and send the images to the processor.

In step 308 the processor compares the occluded-light images of each quadrant of the part to standard dimensional values and tolerances for the part.

In step 310 the processor compares the reflected-light images of the part against visual standards for the part.

In step 312 the processor determines if the part conforms to the dimensional and visual standards. If "yes," the part is blown off into the "good parts bin." If "no," the part is routed to the "bad parts bin."

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of optically inspecting parts, each of the parts of a type having a length, a width, an axis and a head with an underside bearing surface, the method comprising:
   feeding the part onto an angulated, split track configured as a pair of glide rails separated by a gap, to suspend the part on the rails by its underside bearing surface, the track
   having sufficient angulation to permit the part to glide on the rails to an inspection station by gravitational force;
   simultaneously imaging at the inspection station a plurality of exterior side surfaces of the part which are angularly spaced about the axis of the part to form an optical image of at least a portion of each of the imaged side surfaces of the part;
   detecting the optical images;
   processing the detected optical images to obtain a plurality of views of the part which are the angularly spaced about the axis of the part; and
   routing the part after inspection to an unloading station.

2. A system for optically inspecting manufactured parts, each of the manufactured parts of the type having a length, a width, an axis and a head with an underside bearing surface, the system comprising:
   an angulated, split track configured as a pair of parallel glide rails separated by a gap, to suspend a part on the rails by its underside bearing surface, the track having sufficient angulation to permit the part to glide on the rails to an inspection station under gravitational force;
   an imaging assembly at the inspection station to simultaneously image a plurality of exterior side surfaces of the part which are angularly spaced about the axis of the part when the part is located at the inspection station, the assembly including a detector assembly to simultaneously form an optical image of at least a portion of each of the imaged side surfaces of the part and to detect the optical images; and
   a processor to process the detected optical images to obtain a plurality of views of the part which are the angularly spaced about the axis of the part.

3. The system as claimed in claim 2 wherein the glide rails have metal surfaces for contacting the underside bearing surface of the manufactured part head.

4. The system as claimed in claim 3 wherein the glide rails have stainless steel surfaces for contacting the underside bearing surface of the manufactured part head.

5. The system as claimed in claim 2 wherein a surfaces of the glide rails contacting the underside bearing surface of the manufactured part head have a friction-reducing coating.

6. The system as claimed in claim 5 wherein the surfaces of the glide rails contacting the underside bearing surface of the manufactured part head have the friction-reducing coating of a boron-based formulation.

7. The system as claimed in claim 2 wherein the glide rails include material of sufficient transparency to permit viewing of the underside bearing surface at the inspection station.

8. The system as claimed in claim 2 wherein the glide rails are formed of parallel filamentary material.

9. The system as claimed in claim 2 wherein the track is mounted within a frame, and the angle of the track is adjustable by a hinged connection to the frame.

10. The system as claimed in claim 9 wherein one end of the track has a fixed vertical position relative to the frame and the vertical position of the other end of the track is adjustable through a height-adjustment mechanism connected to the frame.

11. The system as claimed in claim 2 wherein the processor capability includes performing a comparison of one or more of the plurality of views of the manufactured part to determine if a part parameter or property is within a range of acceptable values.

12. The system as claimed in claim 2 wherein the gap dimension is adjustable by an adjustment mechanism for controlling the separation of the glide rails to accommodate parts of differing widths.

13. The system as claimed in claim 2 further wherein the track terminus is after the inspection station.

14. The system as claimed in claim 2 further including a reject mechanism responsive to a signal from the processor for controlling a routing of conforming parts and non-conforming parts after each part exits the track.

15. The system as claimed in claim 14 further including an air blow off device for selective routing of each part after it exits the track.

16. The system as claimed in claim 2 further including an overhead camera for imaging a top surface of the part and providing the image to the processor to determine if the part conforms to a predetermined criterion for a physical property of the part head.

17. The system as claimed in claim 16 wherein the overhead camera includes a pericentric lens for viewing the top and side surfaces of the part head.

18. The system as claimed in claim 16 wherein the gap dimension is adjustable by a mechanism for controlling the separation of the glide rails to accommodate parts of differing widths, and the overhead camera is coupled to the mechanism through gears that move the overhead camera an amount proportionate to the adjustment of the gap dimension to keep the overhead camera properly positioned over the part in the inspection station.

19. The system as claimed in claim 2 further including an illumination source at the inspection station, and wherein the gap dimension is adjustable by a mechanism for controlling the separation of the glide rails to accommodate parts of differing widths, and the illumination source is coupled to the mechanism through gears that move the illumination source an amount proportionate to the adjustment of the gap dimension to properly position the illumination source relative to the part in the inspection station.

20. A system for optically inspecting parts, each of the parts of a type having a length, a width, an axis and a head with an underside bearing surface, the system comprising:
    an angulated, split track, configured as a pair of parallel glide rails separated by a gap, to suspend a part on the rails by its underside bearing surface, the gap width being adjustable by an adjustment mechanism so the part head has a width greater than the width of the gap, and the track having an adjustable hinged connection to a supporting frame to permit selection of an angle that allows the part to glide on the rails to an inspection station under gravitational force;
    an imaging assembly at the inspection station to simultaneously image a plurality of exterior side surfaces of the part which are angularly spaced about the axis of the part when the part is located at the inspection station, the assembly including a detector assembly to simultaneously form an optical image of at least a portion of each of the imaged side surfaces of the part and to detect the optical images;
    a processor to process the detected optical images to obtain a plurality of views of the part which are the angularly spaced about the axis of the part and perform a comparison of one or more of the plurality of views of the inspected part to determine if the part conforms to a predetermined criterion for a physical property of the part; and
    a reject mechanism responsive to a signal from the processor for controlling routing of conforming parts and non-conforming parts after each part exits the track.

21. A high-speed method of inspecting manufactured parts of a type having a head with an underside surface and sorting the inspected parts, the method comprising the steps of:
    consecutively transferring a stream of the parts suspended by their underside surfaces in rapid succession from a load station so that the suspended parts travel along the path which extends from the load station through at least one inspection station including a vision station at which exterior side surfaces of the each part which are angularly spaced about an axis of the part and the underside surface of the head are at least temporarily, substantially visually unobstructed and from the vision station to an unload station;
    illuminating the exterior side surfaces and the underside surface of the each part with radiant energy when the each part is at least temporarily, substantially visually unobstructed in the vision station to obtain sets of reflected and unreflected radiation signals;
    detecting and processing the sets of reflected and unreflected radiation signals for the each part to identify parts having unacceptable part characteristics or defects; and
    sorting the parts at the unload station based on the inspection.

22. The method as claimed in claim 21, wherein the underside surface of each of the parts is a bearing surface and wherein the parts slide on their respective bearing surface by a force of gravity.

23. The method as claimed in claim 22 further comprising the step of feeding the parts onto an angulated, split track configured as a pair of glide rails separated by a gap at the load station to suspend the parts on the rails by their underside bearing surfaces, the track having sufficient angulation to permit the parts to slide on the rails to the vision station by gravitational force.

24. The method as claimed in claim 23, wherein the gap between the rails is adjustable to accommodate different sized parts.

25. The method as claimed in claim 23, wherein the glide rails include a transparent window to suspend the part in a generally vertical orientation at the vision station at which the underside surface of the each part has a position and orientation for optical inspection and wherein the method further comprises illuminating the underside surface of the each part through the window with radiant energy at the vision station to obtain reflected radiation signals which are reflected off the underside surface of the part and which the reflected radiation signals travel through the window.

26. The method as claimed in claim 21, wherein the each part is at least partially conductive or semiconductive and wherein the method further comprises inducing an eddy current in the each part, and sensing the induced eddy current to obtain electrical signals.

27. The method as claimed in claim 26, further comprising processing the electrical signals to identify the part as having a metallurgical defect.

28. A high-speed system for inspecting manufactured parts of a type having a head with an underside surface and sorting the inspected parts, the system comprising:
    an angulated split track to consecutively transfer a stream of the parts suspended by their underside surfaces in rapid succession from a load station so that the suspended parts travel along a path which extends from the load station through at least one inspection station including a vision station at which exterior side surfaces of each part which are angularly spaced about an axis of the part and the underside surface of the head are at least temporarily, substantially visually unobstructed and from the vision station to an unload station;
    a plurality of illumination sources to illuminate the exterior side surfaces and the underside surface of the each part with radiant energy when the each part is at least temporarily, substantially visually unobstructed in the vision station to obtain sets of reflected and unreflected radiation signals;
    a plurality of cameras to detect the sets of reflected and unreflected radiation signals for the each part;
    at least one processor to identify the parts having unacceptable part characteristics or defects based on the detected signals; and
    a sorter to sort the parts at the unload station based on the inspection.

29. The system as claimed in claim 28, wherein the underside surface of each of the parts is a bearing surface and wherein the parts slide on their respective bearing surfaces by the force of gravity.

30. The system as claimed in claim 29 further comprising a feeder to feed the parts onto the split track, the split track being configured as a pair of glide rails separated by a gap at the load station to suspend the parts on the rails by their underside bearing surfaces, the track having sufficient angulation to permit the parts to slide on the rails to the vision station by gravitational force.

31. The system as claimed in claim 30, wherein the gap between the rails is adjustable to accommodate different sized parts.

32. The system as claimed in claim 30, wherein the glide rails include a transparent window to suspend the part in a generally vertical orientation at the vision station at which the underside surface of the each part has a position and orientation for optical inspection and wherein the one of the illuminating sources illuminates the underside surface of the each part through the window with radiant energy at the vision station to obtain reflected radiation signals which are reflected off the underside surface of the part and which reflected radiation signals travel through the window.

33. The system as claimed in claim 28, wherein the each part is at least partially conductive or semiconductive and wherein the system further comprises an eddy current sensor to induce an eddy current in the each part and sense the induced eddy current to obtain electrical signals.

34. The system as claimed in claim 33, wherein the at least one processor processes the electrical signals to identify the part as having a metallurgical defect.

\* \* \* \* \*

UNITED STATES PATENT AND TRADEMARK OFFICE
CERTIFICATE OF CORRECTION

PATENT NO. : 10,088,431 B2
APPLICATION NO. : 15/636996
DATED : October 2, 2018
INVENTOR(S) : Robert Joseph Offenborn et al.

Page 1 of 1

It is certified that error appears in the above-identified patent and that said Letters Patent is hereby corrected as shown below:

In the Claims

Column 31, Lines 47-48, Claim 1:
After "views of the part which are"
Delete "the".

Column 31, Line 52, Claim 2:
After "each of the manufactured parts of"
Delete "the" and
Insert -- a --.

Column 32, Line 2, Claim 2:
After "views of the part which are"
Delete "the" .

Column 32, Line 10, Claim 5:
After "claimed in claim 2 wherein"
Delete "a" and
Insert -- the --.

Column 33, Line 22, Claim 20:
After "of the part which are"
Delete "the".

Signed and Sealed this
Twelfth Day of March, 2019

Andrei Iancu
*Director of the United States Patent and Trademark Office*